(12) United States Patent
Adair et al.

(10) Patent No.: US 6,506,881 B1
(45) Date of Patent: *Jan. 14, 2003

(54) ANTI-HMFG ANTIBODIES AND PROCESSES FOR THEIR PRODUCTION

(75) Inventors: John Robert Adair, High Wycombe (GB); Raymond John Owens, Henley-on-Thames (GB); Terence Seward Baker, Wraysbury (GB); Alan Howard Lyons, Maidenhead (GB)

(73) Assignee: Celltech R&D Limited, Slough (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/450,809

(22) Filed: May 25, 1995

Related U.S. Application Data

(63) Continuation of application No. 07/948,541, filed on Sep. 22, 1992.

(30) Foreign Application Priority Data

Sep. 26, 1991 (GB) .............................. 9120467

(51) Int. Cl.[7] .......................... C12P 21/08; C07K 16/30
(52) U.S. Cl. ............................. 530/387.3; 530/387.1; 530/387.7; 530/388.8; 530/388.85
(58) Field of Search ................... 536/23.53; 530/387.1; 435/240.2–240.7, 70.21, 69.7, 252.3, 320.1, 387.3, 387.7, 388.8, 388.85

(56) References Cited

U.S. PATENT DOCUMENTS 5,530,101 A 6/1996 Queen et al. ............. 530/387.3
5,585,089 A 12/1996 Queen et al. ............. 424/133.1

FOREIGN PATENT DOCUMENTS

EP 0239400 * 9/1987 .......... C12N/15/00

OTHER PUBLICATIONS

Panka, D.J. et al. Variable region framework differences result in decrease or increased affinity of variant anti-digoxin antibodies. Proc. Natl. Acad. Sci, USA, 85: 3080–3084, 1988.*
Rudikoff, S. et al. Single amino acid substitution altering antigen–binding specificity. Proc. Natl. Acad. Sci, USA, 79: 1979–1983, 1982.*
Harris TibTech 11:42–46 1993.*
Queen Et Al PNAS 86:10029–10033 1989.*
Riechmann Et Al Nature 332:323–327 1988.*
Kohler and Milstein, *Nature* 1975, 256, 495–497.
Begent et al., *Br. J. Cancer* 1990, 62, 487.
Tempest et al., *Biotechnology* 1991, 9, 266–271.
Co et al., *Proc Natl Acad Sci USA* 1991, 88, 2869–2873.
Verhoeyen et al., "Monoclonal Antibodies: Applications in Clinical Oncology", Epenetos, A.A. 1991.
Gorman et al., *Proc Natl Acad Sci USA* 1991, 88, 4181–4185.
Levy and Miller, *Ann Rev Med* 1983, 34, 107–116.
Schlom and Weeks, Important Advances in Oncology, Lippincott, Philadelphia, 1985, 170–192.
Sahagan et al., *J Immunol* 1986, 137(3), 1066–1074.
Nishimura et al., *Cancer Res* 1987, 47, 999–1005.
Aboud–Pirak et al., *Cancer Res* 1988, 48, 3188–3196.
Orlandi et al., *Proc Natl Acad Sci USA* 1989, 86, 3833–3837.
Max et al., *J Biol Chem* 1981, 256, 5116–5120.

* cited by examiner

*Primary Examiner*—Anthony C. Caputa
*Assistant Examiner*—Anne L. Holleran
(74) *Attorney, Agent, or Firm*—Woodcock Washburn LLP

(57) ABSTRACT

Humanized antibody molecules (HAMs) are described having specificity for human milk fat globule and having an antigen binding site wherein at least one of the complementarity determining regions (CDRs) of the variable domains is derived from the mouse monoclonal antibody CTMO1 and the remaining immunoglobulin-derived parts of the HAM are derived from a human immunoglobulin. The HAMs may be chimeric humanized antibodies or CDR-grafted humanized antibodies and are preferably produced by recombinant DNA techniques. The HAMs are useful for in vivo diagnosis and therapy.

3 Claims, 11 Drawing Sheets

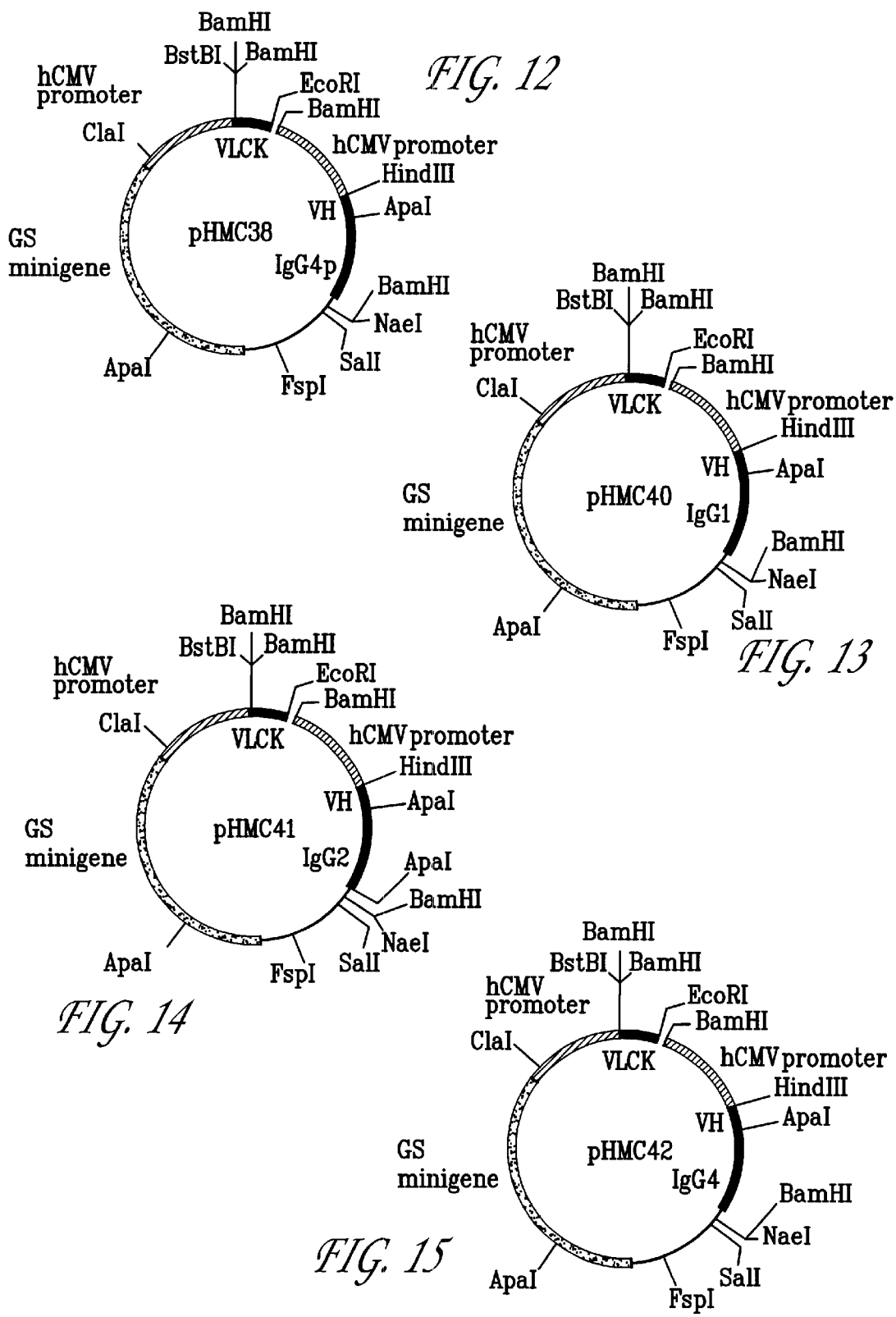

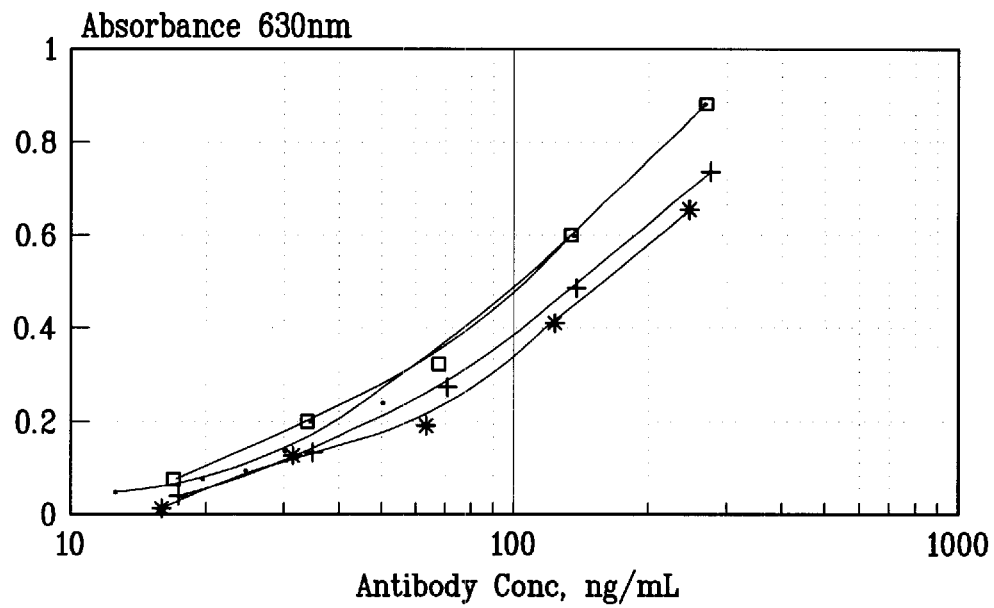
FIG. 22 Direct Binding ELISA: Anti-PEM Activity of Chimeric CTM01 Subclass Series
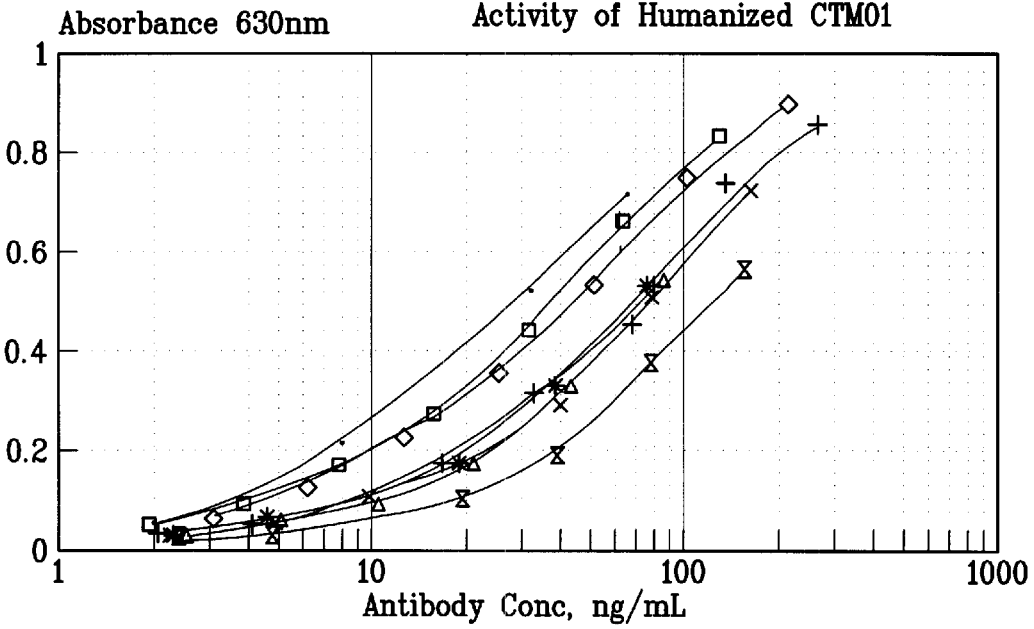
FIG. 23 Direct Binding ELISA: Anti-milk PEM Activity of Humanized CTM01

Comparison of the antitumor activity of hu:CT-M-01 & Murine CT-M-01 Conjugates of the hydroxysuccinimide derivative of 4-mercapto-4-methyl-pentanoic acid disulfide of N-acetyl calicheamicin $\gamma_1^I$ vs. OvCar3 (Ovarian)

US 6,506,881 B1

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 416
      (B) TYPE: nucleic acid (C) STRANDEDNESS: single
        (D) TOPOLOGY: linear (xi) SEQUENCE DESCRIPTION: SEQ ID NO: 1:

```
ATG GAA TGG AGC TGG GTC TTT CTC TTC TTC CTG TCG GTA ACC ACA GGT        48
Met Glu Trp Ser Trp Val Phe Leu Phe Phe Leu Ser Val Thr Thr Gly
5                   10                  15

GTC CAT TGC CAG ATC CAG CTG CAG CAG TCT GGA CCT GAG CTG GTG AAG        96
Val His Cys Gln Ile Gln Leu Gln Gln Ser Gly Pro Glu Leu Val Lys
20                  25                  30

CCT GGG GCT TCA GTG AAG ATA TCC TGC AAG GCT TCT GGC TAC ACC TTC       144
Pro Gly Ala Ser Val Lys Ile Ser Cys Lys Ala Ser Gly Tyr Thr Phe
35                  40                  45

ACT GAC TAC TAT ATA AAC TGG ATG AAG CAG AAG CCT GGA CAG GGA CTT       192
Thr Asp Tyr Tyr Ile Asn Trp Met Lys Gln Lys Pro Gly Gln Gly Leu
50                  55                  60

GAG TGG ATT GGA TGG ATT GAT CCT GGA AGC GGT AAT ACT AAG TAC AAT       240
Glu Trp Ile Gly Trp Ile Asp Pro Gly Ser Gly Asn Thr Lys Tyr Asn
65                  70                  75                  80

GAG AAG TTC AAG GGC AAG GCC ACA TTG ACT GTA GAC ACA TCC TCC AGC       288
Glu Lys Phe Lys Gly Lys Ala Thr Leu Thr Val Asp Thr Ser Ser Ser
85                  90                  95

ACA GCC TAC ATG CAG CTC AGC AGC CTG ACA TCT GAG GAC ACT GCT GTC       336
Thr Ala Tyr Met Gln Leu Ser Ser Leu Thr Ser Glu Asp Thr Ala Val
100                 105                 110

TAT TTC TGT GCA AGA GAG AAA ACG ACC TAT TAC TAT GCT ATG GAC TAC       384
Tyr Phe Cys Ala Arg Glu Lys Ile Thr Tyr Tyr Tyr Ala Met Asp Tyr
115                 120                 125

TGG GGT CAA GGA ACC TCA GTC ACT GTC TCC GC                            416
Trp Gly Gln Gly Thr Ser Val Thr Val Ser Ala
130                 135
```

(2) INFORMATION FOR SEQ ID NO: 2:

(i) SEQUENCE CHARACTERISTICS:
        (A) LENGTH: 399
        (B) TYPE: nucleic acid
        (C) STRANDEDNESS: single
        (D) TOPOLOGY: linear (xi) SEQUENCE DESCRIPTION: SEQ ID NO: 2:

```
ATG AGG TGC CTA GCT GAG TTC CTG GGG CTG CTT GTG CTC TGG ATC CCT        48
Met Arg Cys Leu Ala Glu Phe Leu Gly Leu Leu Val Leu Trp Ile Pro
5                   10                  15

GGA GCC ATT GGG GAT ATT GTG ATG ACT CAG GCT GCA CCC TCT GTT CCT        96
Gly Ala Ile Gly Asp Ile Val Met Thr Gln Ala Ala Pro Ser Val Pro
20                  25                  30

GTC ACT CCT GGA GAG TCA TTA TCC ATT TCC TGC AGG TCT AGT AAG AGT       144
Val Thr Pro Gly Glu Ser Leu Ser Ile Ser Cys Arg Ser Ser Lys Ser
35                  40                  45

CTC CTT CAT AGT AAT GGC GAC ACT TTC TTG TAT TGG TTC CTG CAG AGG       192
Leu Leu His Ser Asn Gly Asp Thr Phe Leu Tyr Trp Phe Leu Gln Arg
50                  55                  60

CCA GGC CAG TCT CCT CAA CTC CTG ATA TAT CGG ATG TCC AAC CTT GCC       240
Pro Gly Gln Ser Pro Gln Leu Leu Ile Tyr Arg Met Ser Asn Leu Ala
65                  70                  75                  80

TCC GGA GTC CCA GAC AGG TTC AGT GGC AGT GGG TCA GGA ACT GCT TTC       288
Ser Gly Val Pro Asp Arg Phe Ser Gly Ser Gly Ser Gly Thr Ala Phe
85                  90                  95

ACA CTG AGA GTC AGT AGA GTG GAG GCT GAG GAT GTG GGT GTT TAT TAC       336
Thr Leu Arg Val Ser Arg Val Glu Ala Glu Asp Val Gly Val Tyr Tyr
100                 105                 110
```

```
TGT ATG CAA CAT CTA GAA TAT CCT TTC ACG TTC GGT GCT GGG ACC AAG       384
Cys Met Gln His Leu Glu Tyr Pro Phe Tyr Phe Gly Ala Gly Thr Lys
115                 120                 125

CTG GAG CTG AAA CGG                                                   399
Leu Gly Leu Lys Arg
130
```

(2) INFORMATION FOR SEQ ID NO: 3:

(i) SEQUENCE CHARACTERISTICS:
        (A) LENGTH: 28
        (B) TYPE: nucleic acid
        (C) STRANDEDNESS: single
        (D) TOPOLOGY: linear (xi) SEQUENCE DESCRIPTION: SEQ ID NO: 3:

```
GGTGGCG   GTA  ACC  ACA  GGT  GTC  CAG   TCA                          28
Val Thr   Thr  Gly  Val  Gln  Ser
5
```

(2) INFORMATION FOR SEQ ID NO: 4:

(i) SEQUENCE CHARACTERISTICS:
        (A) LENGTH: 36
        (B) TYPE: nucleic acid
        (C) STRANDEDNESS: single
        (D) TOPOLOGY: linear (xi) SEQUENCE DESCRIPTION: SEQ ID NO: 4:

```
AGTGGCAGAG   AAGTCGGAGT   TGCTTCCCGG   GTAGAC                         36
```

(2) INFORMATION FOR SEQ ID NO: 5:

(i) SEQUENCE CHARACTERISTICS:
        (A) LENGTH: 50
        (B) TYPE: nucleic acid
        (C) STRANDEDNESS: double
        (D) TOPOLOGY: linear (xi) SEQUENCE DESCRIPTION: SEQ ID NO: 5:

```
AGCTTGCCGC CACC ATG GAA TGG AGC TGG GTC TTT CTC TTC TTC CTG TCG       50
             Met Glu Trp Ser Trp Val Phe Leu Phe Phe Leu Ser
                  5                   10
```

(2) INFORMATION FOR SEQ ID NO: 6:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 6:

```
GCGCGCAAGC   TTGCCGCCAC   C                                           21
```

(2) INFORMATION FOR SEQ ID NO: 7:

(i) SEQUENCE CHARACTERISTICS:
        (A) LENGTH: 96
        (B) TYPE: nucleic acid
        (C) STRANDEDNESS: single
        (D) TOPOLOGY: linear (xi) SEQUENCE DESCRIPTION: SEQ ID NO: 7:

```
TCTCAGATTC AGCTGGTGCA GTCTGGAGCA GAGGTGAAGA AGCCTGGATC                50
TTCTGTGAAG GTGTCTTGTA AGGCATCTGG ATACACCTTC ACCGAC                    96
```

(2) INFORMATION FOR SEQ ID NO: 8:

(i) SEQUENCE CHARACTERISTICS:
       (A) LENGTH: 96
       (B) TYPE: nucleic acid
       (C) STRANDEDNESS: single
       (D) TOPOLOGY: linear (xi) SEQUENCE DESCRIPTION: SEQ ID NO: 8:

```
TGGATTGACC CTGGATCTGG AAATACAAAG TACAATGAGA AGTTCAAGGG        50

AAGAGTGACA ATTACAGTGG ACACATCCAC GAATACCGCC TACATG           96
```

(2) INFORMATION FOR SEQ ID NO: 9:

(i) SEQUENCE CHARACTERISTICS:
       (A) LENGTH: 89
       (B) TYPE: nucleic acid
       (C) STRANDEDNESS: single
       (D) TOPOLOGY: linear (xi) SEQUENCE DESCRIPTION: SEQ ID NO: 9:

```
GAGAAGACCA CCTACTACTA CGCAATGGAC TACTGGGGAC AGGGAACACT        50

GGTGACAGTG TCTTCTGCCT CAACGAAGGG CCCGCGCGC                   89
```

(2) INFORMATION FOR SEQ ID NO: 10:

(i) SEQUENCE CHARACTERISTICS:
       (A) LENGTH: 96
       (B) TYPE: nucleic acid
       (C) STRANDEDNESS: single
       (D) TOPOLOGY: linear (xi) SEQUENCE DESCRIPTION: SEQ ID NO: 10:

```
CTGCACCAGC TGAATCTGAG AATGGACTCC TGTAGTTACT GACAGGAAGA        50

AGAGAAAGAC CCAGCTCCAT TCCATGGTGG CGGCAAGCTT GCGCGC           96
```

(2) INFORMATION FOR SEQ ID NO: 11:

(i) SEQUENCE CHARACTERISTICS:
       (A) LENGTH: 96
       (B) TYPE: nucleic acid
       (C) STRANDEDNESS: single
       (D) TOPOLOGY: linear (xi) SEQUENCE DESCRIPTION: SEQ ID NO: 11:

```
TCCAGATCCA GGGTCAATCC ATCCCATCCA CTCGAGTCCC TGTCCAGGTG        50

CCTGTCTCAT CCAATTAATG TAGTAGTCGG TGAAGGTGTA TCCAGA           96
```

(2) INFORMATION FOR SEQ ID NO: 12:

(i) SEQUENCE CHARACTERISTICS:
       (A) LENGTH: 93
       (B) TYPE: nucleic acid
       (C) STRANDEDNESS: single
       (D) TOPOLOGY: linear (xi) SEQUENCE DESCRIPTION: SEQ ID NO: 12:

```
GTAGTAGTAG GTGGTCTTCT CTCTTGCACA GAAGTAGAAT GCTGTGTCCT        50

CAGATCTCAG AGAAGACAGC TCCATGTAGG CGGTATTCGT GGA              93
```

(2) INFORMATION FOR SEQ ID NO: 13:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 13:

```
GCGCGCGGGC  CCTTCGTTGA       G                                        21
```

(2) INFORMATION FOR SEQ ID NO: 14:

(i) SEQUENCE CHARACTERISTICS:
        (A) LENGTH: 139
        (B) TYPE: amino acid
        (D) TOPOLOGY: linear (xi) SEQUENCE DESCRIPTION: SEQ ID NO: 14:

```
Met Glu Trp Ser Trp Val Phe Leu Phe Leu Ser Val Thr Thr
  5                  10                  15
Gly Val His Ser Gln Ile Gln Leu Val Gln Ser Gly Ala Glu Val
 20                  25                  30
Lys Lys Pro Gly Ser Ser Val Lys Val Ser Cys Lys Ala Ser Gly
 35                  40                  45
Tyr Thr Phe Thr Asp Tyr Tyr Ile Asn Trp Met Arg Gln Ala Pro
 50                  55                  60
Gly Gln Gly Leu Glu Trp Met Gly Trp Ile Asp Pro Gly Ser Gly
 65                  70                  75
Asn Thr Lys Tyr Asn Glu Lys Phe Lys Gly Arg Val Thr Ile Thr
 80                  85                  90
Val Asp Thr Ser Thr Asn Thr Ala Tyr Met Glu Leu Ser Ser Leu
 95                 100                 105
Arg Ser Glu Asp Thr Ala Phe Tyr Phe Cys Ala Arg Glu Lys Thr
110                 115                 120
Thr Tyr Tyr Tyr Ala Met Asp Tyr Trp Gly Gln Gly Thr Leu Val
125                 130                 135
Thr Val Ser Ser
139
```

(2) INFORMATION FOR SEQ ID NO: 15:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 15:

```
GGACTGTTCG  AAGCCGCCAC       C                                        21
```

(2) INFORMATION FOR SEQ ID NO: 16:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO: 16:

```
TGGCTTACAG  ATGCCAGATG  CGATATCCAG  ATGACTCAGA  GTCCAAGTAC            50
TCTCAGTGCC  AGTGTAGGTG  ATAGGGTCAC  C                                 81
```

(2) INFORMATION FOR SEQ ID NO: 17:

(i) SEQUENCE CHARACTERISTICS:
        (A) LENGTH: 90
        (B) TYPE: nucleic acid
        (C) STRANDEDNESS: single
        (D) TOPOLOGY: linear (xi) SEQUENCE DESCRIPTION: SEQ ID NO: 17:

```
GGTGACACCT  TCCTCTATTG  GTTCCAGCAG  AAACCAGGTA  AAGCCCCAAA         50

GCTCCTCATG  TATAGGATGA  GTAACCTCGC  CAGTGGTGTA                     90
```

(2) INFORMATION FOR SEQ ID NO: 18:

(i) SEQUENCE CHARACTERISTICS:
        (A) LENGTH: 99
        (B) TYPE: nucleic acid
        (C) STRANDEDNESS: single
        (D) TOPOLOGY: linear (xi) SEQUENCE DESCRIPTION: SEQ ID NO: 18:

```
CAGCCAGATG  ATTTCGCCAC  TTATTATTGT  ATGCAGCATC  TCGAATATCC         50

ATTCACTTTC  GGTCAGGGTA  CTAAAGTAGA  AGTAAAACGT  ACGGGCCGG          99
```

(2) INFORMATION FOR SEQ ID NO: 19:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO: 19:

```
GCATCTGGCA  TCTGTAAGCC  ACAGCAGCAG  GAGTCCGAGG  ACTTGGGTGG         50

GGACAGACAT  GGTGGCGGCT  TCGAACAGTC  C                              81
```

(2) INFORMATION FOR SEQ ID NO: 20:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO: 20:

```
CCAATAGAGG  AAGGTGTCAC  CGTTACTATG  GAGGAGACTT  TTACTACTCC         50

TACAAGTGAT  GGTGACCCTA  TCACCTACAC  T                              81
```

(2) INFORMATION FOR SEQ ID NO: 21:

(i) SEQUENCE CHARACTERISTICS:
        (A) LENGTH: 102
        (B) TYPE: nucleic acid
        (C) STRANDEDNESS: single
        (D) TOPOLOGY: linear (xi) SEQUENCE DESCRIPTION: SEQ ID NO: 21:

```
AGTGGCGAAA  TCATCTGGCT  GGAGACTACT  GATAGTGAGA  GTGAACTCAG         50

TACCACTACC  ACTACCACTG  AATCTAGATG  GTACACCACT  GGCGAGGTTA        100

CT                                                                102
```

-continued (2) INFORMATION FOR SEQ ID NO: 22:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 22:

CCGGCCCGTA CGTTTTACTT C                    21

(2) INFORMATION FOR SEQ ID NO: 23:

(i) SEQUENCE CHARACTERISTICS:
        (A) LENGTH: 133
        (B) TYPE: amino acid
        (D) TOPOLOGY: linear (xi) SEQUENCE DESCRIPTION: SEQ ID NO: 23:

```
Met Ser Val Pro Thr Gln Val Leu Gly Leu Leu Leu Leu Trp Leu
 5               10                  15

Thr Asp Ala Arg Cys Asp Ile Gln Met Thr Gln Ser Pro Ser Thr
20                  25                  30

Leu Ser Ala Ser Val Gly Asp Arg Val Thr Ile Thr Cys Arg Ser
35                  40                  45

Ser Lys Ser Leu Leu His Ser Asn Gly Asp Thr Phe Leu Tyr Trp
50                  55                  60

Phe Gln Gln Lys Pro Gly Lys Ala Pro Lys Leu Leu Met Tyr Arg
65                  70                  75

Met Ser Asn Leu Ala Ser Gly Val Pro Ser Arg Phe Ser Gly Ser
80                  85                  90

Gly Ser Gly Thr Glu Phe Thr Leu Thr Ile Ser Ser Leu Gln Pro
95                  100                 105

Asp Asp Phe Ala Thr Tyr Tyr Cys Met Gln His Leu Glu Tyr Pro
110                 115                 120

Phe Thr Phe Gly Gln Gly Thr Lys Val Glu Val Lys Arg
125                 130
```

(2) INFORMATION FOR SEQ ID NO: 24:

(i) SEQUENCE CHARACTERISTICS:
        (A) LENGTH: 51
        (B) TYPE: nucleic acid
        (C) STRANDEDNESS: double
        (D) TOPOLOGY: linear (xi) SEQUENCE DESCRIPTION: SEQ ID NO: 24:

ACGGCGGTGG TACCTTACCT CGACCCAGAA AGAGAAGAAGGACAGCCATT G        51

ANTI-HMFG ANTIBODIES AND PROCESSES FOR THEIR PRODUCTION

This is a continuation, of application Ser. No. 07/948,541, filed Sep. 22, 1992.

FIELD OF THE INVENTION

The present invention relates to humanised antibody molecules (HAMs) having specificity for human milk fat globule (HMFG) and to processes for their production using recombinant DNA technology.

BACKGROUND TO THE INVENTION

The term "humanised antibody molecule" (HAM) is used to describe a molecule having an antigen binding site derived from an immunoglobulin from a non-human species, the remaining immunoglobulin-derived parts of the molecule being derived from a human immunoglobulin. The antigen binding site may comprise: either a complete variable domain from the non-human immunoglobulin fused onto one or more human constant domains; or one or more of the complementarity determining regions (CDRs) grafted onto appropriate human framework regions in the variable domain. The abbreviation "MAb" is used to indicate a monoclonal antibody.

In the description, reference is made to publications by number. These numbers are placed in square brackets [ ]. The publications are listed in numerical order at the end of the description.

Natural immunoglobulins have been known for many years, as have the various fragments thereof, such as the Fab, Fab' (Fab')$_2$ and Fc fragments, which can be derived by enzymatic cleavage. Natural immunoglobulins comprise a generally Y-shaped molecule having an antigen-binding site towards the outer end of each arm. The remainder of the structure, and particularly the stem of the Y, mediates the effector functions associated with immunoglobulins.

Natural immunoglobulins have been used in assay, diagnosis and, to a more limited extent, therapy. However, such uses, especially in therapy, have been hindered by the polyclonal nature of natural immunoglobulins. A significant step towards the realisation of the potential of immunoglobulins as therapeutic agents was the discovery of procedures for the production of monoclonal antibodies of defined specificity [1]. However, most MAbs are produced by hybridomas which are fusions of rodent spleen cells with rodent myeloma cells. The resultant MAbs are therefore essentially rodent proteins. There are few reports of the production of human MAbs.

Since most available MAbs are of rodent origin, they are naturally antigenic in humans and thus can give rise to an undesirable immune response termed the HAMA (Human Anti-Mouse Antibody) response. Therefore, the use of rodent MAbs as therapeutic agents in humans is inherently limited by the fact that the human subject will mount an immunological response to the MAb and will either remove it entirely or at least reduce its effectiveness.

Therefore proposals have been made for making non-human MAbs less antigenic in humans. Such techniques can be generically termed "humanisation" techniques. These techniques generally involve the use of recombinant DNA technology to manipulate DNA sequences encoding the polypeptide chains of the antibody molecule.

Early methods for humanising MAbs related to production of chimeric antibodies in which an antigen binding site comprising the complete variable domains of one antibody are fused to constant domains derived from a second antibody. Methods for carrying out such chimerisation procedures are described in EP-A-0 120 694 (Celltech Limited), EP-A-0 125 023 (Genentech Inc.), EP-A-0 171 496 (Res. Dev. Corp. Japan), EP-A-0173494 (Stanford University) and EP-A-0 194 276 (Celltech Limited).

EP-A-0 194 276 discloses a process for preparing an antibody molecule having the variable domains from a mouse MAb and the constant domains from a human immunoglobulin. It also describes the production of an antibody molecule comprising the variable domains of a mouse MAb, the CH1 and CL domains of a human immunoglobulin and a non-immunoglobulin-derived protein in place of the Fc portion of the human immunoglobulin.

Subsequently, a number of further patent applications have been published relating to chimeric antibodies, including tumour specific chimeric antibodies. Among these applications are WO-A-87/02671 (Int. Gen. Eng. Inc.), EP-A-0 256 654 (Centocor), EP-A-0 266 663 (Int. Gen. Eng. Inc. & Oncogen), WO-A-89/00999 (Int. Gen. Eng. Inc.) and EP-A-0 332 424 (Hybritech Inc.).

Such humanised chimeric antibodies, however, still contain a significant proportion of non-human amino acid sequence, i.e. the complete variable domains. Thus, such humanised antibodies may elicit some HAMA response, particularly if administered over a prolonged period [2].

In an alternative approach, described in EP-A-0 239 400 (Winter), the complementarity determining regions (CDRs) of a mouse MAb have been grafted onto the framework regions of the variable domains of a human immunoglobulin by site directed mutagenesis using long oligonucleotides. Such CDR-grafted humanised antibodies are less likely to give rise to a HAMA response than humanised chimeric antibodies in view of the lower proportion of non-human amino acid sequence which they contain. There are three CDRs (CDR1, CDR2 and CDR3) in each of the heavy and light chain variable domains.

The earliest work on CDR-grafted humanised MAbs was carried out on a MAb recognising the synthetic antigen NP or NIP. However, subsequently, examples in which a mouse MAb recognising lysozyme and a rat MAb recognising an antigen on human T cells respectively were humanised have been described [3, 4]. The preparation of the CDR-grafted antibody to the antigen on human T cells is also described in WO-A-89/07452 (Medical Research Council). Recently the preparation of a humanised CDR-grafted antibody that binds to the interleukin 2 receptor has been described [5]. Further examples of humanised CDR-grated antibodies having specificity for anti-viral [6, 7], anti-tumour [8] and anti-T cell [9 and EP-A-0 403 156] antigens have been described more recently.

Our copending International Patent Specification No. WO-A-91/09967 relates to the CDR grafting of antibodies in general.

It has been widely suggested that immunoglobulins, and in particular MAbs, could potentially be very useful in the diagnosis and treatment of cancer [10, 11]. There has therefore been much activity in trying to produce immunoglobulins or MAbs directed against tumour-specific antigens. So far, over one hundred MAbs directed against a variety of human carcinomas have been used in various aspects of tumour diagnosis or treatment [12].

There have been a number of papers published concerning the production of chimeric monoclonal antibodies recognising cell surface antigens. For instance, genetically engineered murine/human chimeric antibodies which retain specificity for tumour-associated antigens have been described [13 and WO-A-89/01783]. Also, a recombinant murine/human chimeric monoclonal antibody specific for common acute lymphocytic leukaemia antigen has been described [14].

SUMMARY OF THE INVENTION

We have now prepared humanised antibodies to human milk fat globule (HMFG) derived from the anti-HMFG mouse MAb CTMO1 [15].

According to the present invention, there is provided a humanised antibody molecule (HAM) having specificity for human milk fat globule (HMFG) and having an antigen binding site wherein at least one of the complementarity determining regions (CDRs) of the variable domain is derived from the mouse monoclonal antibody CTMO1 (CTMO1 MAb) and the remaining immunoglobulin-derived parts of the HAM are derived from a human immunoglobulin or an analogue thereof.

The HAM may comprise a chimeric humanised antibody or a CDR-grafted humanised antibody. When the HAM comprises a CDR-grafted humanised antibody, each heavy or light chain variable domain may comprise only one or two CTMO1-derived CDRs. Preferably, however, all three heavy and light chain CDRs are derived from CTMO1.

The CTMO1 MAb is a mouse MAb of the type IgG1-kappa raised against the membrane-associated antigen of HMFG and has been extensively studied [15]. The CTMO1 MAb has been shown to recognise breast, ovarian and non-small cell lung cancers. It has been shown to internalise rapidly into target cells. Conjugates of CTMO1 and calichaemicin display highly specific cytotoxicity against appropriate cell lines, (see U.S. Pat. No 5,053,394).

High levels of the antigen recognised by the CTMO1 MAb have been detected circulating in the blood of patients suffering from breast cancer. This may have a deleterious effect on pharmacokinetics and tumour localisation in vivo. However, circulating antigen levels in the blood of patients suffering from ovarian cancer are lower than those in breast cancer patients. It is therefore believed that the HAM of the present invention will be of particular use in the treatment of ovarian cancer.

It is believed that the CTMO1 MAb recognises the polymorphic epithelial mucin (PEM) of HMFG. Thus, preferably, the present invention provides a HAM which recognises the PEM of HMFG.

Surprisingly, it has been found that humanising the CTMO1 MAb does not substantially adversely affect its binding activity or internalisation, and can create, particularly by CDR grafting, a HAM which has better binding and internalisation characteristics than the murine antibody (see Table 1 hereinafter). This produces a HAM which is of use in both therapy and diagnosis of certain human carcinomas, for example carcinomas of ovary, breast, uterus and lung.

Preferably, the HAM of the present invention is produced by recombinant DNA technology.

The HAM of the present invention may comprise: a complete antibody molecule, having full length heavy and light chains; a fragment thereof, such as an Fab, Fab', (Fab')$_2$ or Fv fragment; a single chain antibody fragment, e.g. a single chain Fv; a light chain or heavy chain monomer or dimer; or a fragment or analogue of any of these or any other molecule with the same specificitiy as the CTMO1 MAb.

The HAM of the present invention may have attached to it an effector molecule such as a cytotoxic or cytostatic agent, or a reporter group, for example an atom or molecule such as a radionuclide, or complexed radionuclide capable of being detected while inside the human body. For instance, the HAM may have a macrocycle, for chelating a heavy metal atom, or a toxin, such a ricin, attached to it by a covalent bridging structure. Alternatively, the procedures of recombinant DNA technology may be used to produce a HAM in which the Fc fragment, CH2 or CH3 domain of a complete molecule has been replaced by or has attached thereto by peptide linkage a functional non-immunoglobulin protein, such as an enzyme or toxin molecule.

The remaining non-CTMO1 immunoglobulin-derived parts of the HAM may be derived from a suitable human immunoglobulin. For instance, when the HAM is a CDR-grafted HAM, appropriate variable region framework sequences may be used having regard to the class or type of the CTMO1 donor antibody from which the antigen binding regions are derived. Preferably, the type of human framework used is of the same or similar class or type as the donor antibody (CTMO1 is IgG1-kappa). Advantageously, the framework is chosen to maximise or optimise homology with the donor antibody sequence, particularly at positions spatially close to or adjacent the CDRs. Examples of human frameworks which may be used to construct CDR-grafted HAMs are LAY, POM, TUR, TEI, KOL, NEWM, REI and EU [16]. KOL and NEWM are suitable for heavy chain construction. REI is suitable for light chain construction. EU is particularly suitable for both heavy chain and light chain construction. Preferably, the EU framework is used as the human framework for both heavy and light chain variable domains in view of its high level of homology with the CTMO1 MAb.

The light or heavy chain variable regions of the HAM may be fused to human light or heavy chain constant domains as appropriate, (the term "heavy chain constant domains" as used herein are to be understood to include hinge regions unless specified otherwise). The human constant domains of the HAM, where present, may be selected having regard to the proposed function of the antibody, in particular the effector functions which may be required. For example, the heavy chain constant domains fused to the heavy chain variable region may be human IgA, IgG or IgM domains. Preferably human IgG domains are used. IgG1 and IgG3 isotype domains may be used when the HAM is intended for therapeutic purposes and antibody effector functions are required. Alternatively, IgG2 and IgG4 isotype domains may be used when the HAM is intended for purposes for which antibody effector functions are not required, e.g. for imaging, diagnostic or cytotoxic targeting purposes. Light chain human constant domains which may be fused to the light chain variable region include human Lambda or, especially, human Kappa chains.

Analogues of human constant domains may alternatively be advantageously used. These include those constant domains containing one or more additional amino acids than the corresponding human domain, or those constant domains wherein one or more existing amino acids of the corresponding human domain has been deleted or altered. Such domains may be obtained, for example, by oligonucleotide directed mutagenesis. In the present invention, a particularly useful analogue of a heavy chain constant domain is an IgG4 constant domain in which a serine residue at position 241 of the corresponding naturally occuring human domain has been altered to a proline residue.

The remainder of the HAM need not comprise only protein sequences from human immunoglobulins. For instance, a gene may be constructed in which a DNA sequence encoding part of a human immunoglobulin chain is fused to a DNA sequence encoding the amino acid sequences of a polypeptide effector or reporter molecule.

According to a second aspect of the present invention, there is provided a process for producing the HAM of the first aspect of the invention, which process comprises:

(a) producing in an expression vector an operon having a DNA sequence which encodes an antibody heavy or light chain comprising a variable domain wherein at least one of the CDRs of the variable domain is derived from the CTMO1 MAb and the remaining immunoglobulin-derived parts of the antibody chain are derived from a human immunoglobulin;

(b) producing in an expression vector an operon having a DNA sequence which encodes a complementary antibody light or heavy chain comprising a variable domain wherein at least one of the CDRs of the variable domain is derived from the CTMO1 MAb and the remaining immunoglobulin-derived parts of the antibody chain are derived from a human immunoglobulin;

(c) transfecting a host cell with both operons; and (d) culturing the transfected cell line to produce the HAM.

The cell line may be transfected with two vectors, the first vector containing the operon encoding the light chain-derived polypeptide and the second vector containing the operon encoding the heavy chain-derived polypeptide. Preferably, the vectors are identical except in so far as the coding sequences and selectable markers are concerned so as to ensure as far as possible that each polypeptide chain is equally expressed.

Alternatively, a single vector may be used, the vector including the operons encoding both light chain- and heavy chain-derived polypeptides.

In further aspects, the invention also includes DNA sequences coding for the heavy and light chains of the HAM of the present invention, cloning and expression vectors containing these DNA sequences, host cells transformed with these DNA sequences and processes for producing the heavy or light chains and antibody molecules comprising expressing these DNA sequences in a transformed host cell.

The general methods by which the vectors may be constructed, transfection methods and culture methods are well known per se [17, 18].

The DNA sequences which encode the CTMO1 heavy and light chain variable domain amino acid sequences (and the corresponding deduced amino acid sequences) are given hereinafter in the sequence listing as Sequence ID No. 1 and Sequence ID No. 2 respectively.

DNA coding for human immunoglobulin sequences may be obtained in any appropriate way. For example, amino acid sequences of preferred human acceptor frameworks, such as LAY, POM, KOL, REI, EU, TUR, TEI and NEWM, are widely available to workers in the art. Corresponding DNA sequences which code for these amino acid sequences may be inferred or deduced by reverse application of the genetic code. Similarly, the amino acid sequences of human constant region domains are well known and DNA sequences which code for them may be readily deduced.

The standard techniques of molecular biology may be used to prepare DNA sequences coding for CDR-grafted products. Desired DNA sequences may be synthesised completely or in part using oligonucleotide synthesis techniques. Site-directed mutagenesis and polymerase chain reaction (PCR) techniques may be used as appropriate. For example, oligonucleotide directed synthesis [19] may be used. Also, oligonucleotide directed mutagenesis of a pre-existing variable domain region [3, 4] may be used. Enzymatic filling-in of gapped oligonucleotides using T4 DNA polymerase [5] may be used.

Any suitable host cell/vector system may be used for expression of the DNA sequences coding for the chimeric or CDR-grafted heavy and light chains. Bacterial, e.g. E. coli, and other microbial systems may be used, in particular for expression of antibody fragments, e.g. Fv, Fab and Fab' fragments and single chain antibody fragments, e.g. single chain Fvs. Eucaryotic, e.g. mammalian host cell, expression systems may be used for production of larger chimeric or CDR-grafted antibody products, including complete antibody molecules. Suitable mammalian host cells include CHO cells and myeloma or hybridoma cell lines, for example NSO cells.

The present invention also includes therapeutic and diagnostic compositions containing the HAM of the invention and uses of such compositions in therapy and diagnosis. Such therapeutic and diagnostic compositions typically comprise a HAM according to the invention in combination with a pharmaceutically acceptable excipient, diluent or carrier, e.g. for in vivo use.

Therapeutic and diagnostic uses typically comprise administering an effective amount of a HAM according to the invention to a human subject. The exact dose to be administered will vary according to the intended use of the HAM and on the age and condition of the patient but may be typically varied from about 0.1 mg to 1000 mg, for example from about 1 mg to 500 mg. The HAM may be administered as a single dose, or in a continuous manner over a period of time. Doses may be repeated as appropriate. The HAM may be formulated in accordance with conventional practice for administration by any suitable route, and may generally be in a liquid form [e.g. a solution of the antibody in a sterile physiologically acceptable buffer] for administration by for example an intravenous, intraperitoneal or intramuscular route.

In the HAM of the first aspect of the invention and the process of the second aspect of the invention, the heavy and light chain variable domains of the HAM may comprise either the entire variable domains of the CTMO1 MAb or may comprise framework regions of a human variable domain having grafted thereon one, two or all three of the CDRs of the CTMO1 MAb. Thus, the HAM may comprise a chimeric humanised antibody or a CDR-grafted humanised antibody.

When the HAM is a CDR-grafted humanised antibody, in addition to the CDRs, specific variable region framework residues may be altered to correspond to non-human, i.e. the CTMO1 mouse, residues.

Preferably, the CDR-grafted humanised antibodies of the present invention include CDR-grafted humanised antibodies as defined in our International Patent Specification WO-A-91/09967. The disclosure of WO-A-91/09967 allowed U.S. application Ser. No. 08/303,569, filed Aug. 16, 1991, is incorporated by reference.

Preferably, the CDRs of light chain correspond to the Kabat CTMO1 MAb CDRs at CDR1 (residues 24–34) and CDR2 (residues 50–56) and to the structural loop residues (residues 91–96) or Kabat CTMO1 MAb CDR residues (residues 89–97) in CDR3. (The residue designations given above and elsewhere in the present application are numbered according to the Kabat numbering system [16]). In addition, the light chain may have mouse CTMO1 residues at one or more of residues 1, 2, 3, 36, 37, 45, 48, 49, 60, 63, 70, 84, 85, 87 and 108. In preferred embodiments, when the human framework used is EU, the light chain comprises Kabat CTMO1 MAb CDRs at all of CDR1, CDR2 and CDR3 and preferably additional CTM01 residues at positions 3, 36, 37, 45, 48, 63 and 108, or especially additional CTMO1 residues at positions 3, 36, 63 and 108 only.

Preferably, the CDRs of the heavy chain correspond to the Kabat CTMO1 MAb CDRs at all of CDR1 (26 to 35), CDR2 (50 to 65) and CDR3 (94 to 100). In addition, the heavy chain may have mouse CTMO1 residues at one or more of residues, 2, 6, 23, 37, 48, 49, 67, 69, 73, 76, 78, 80, 88, 91 and 94. In particularly preferred embodiments, when the human framework used is EU, the heavy chain framework comprises additional CTM01 MAb residues at positions 2, 37, 71 and 73, and especially in addition at positions 48, 67 and 69.

In addition, EU has a particularly idiosyncratic J region between residues 103 to 113 and it may be useful to include the murine amino acids, a consensus human J region or a suitable combination of both at residues 103 to 108 inclusive. When the EU framework is used, preferably heavy chain residues 94, 103, 104, 105 and 107 are murine residues, since in the case of these residues, the murine sequence is more frequently found in human VH sequences than the EU residues.

BRIEF DESCRIPTION OF THE DRAWINGS

The present invention is now described, by way of example only, with reference to the accompanying drawings, in which:

FIG. 12 is a schematic diagram of plasmid pHMC38;

FIG. 13 is a schematic diagram of plasmid pHMC40;

FIG. 14 is a schematic diagram of plasmid pHMC41;

FIG. 15 is a schematic diagram of plasmid pHMC42;

FIG. 22 is a graph of a direct binding ELISA on transiently expressed chimeric antibodies;

FIG. 23 is a graph of a direct binding ELISA on transiently expressed CDR-grafted antibodies.

DESCRIPTION OF SPECIFIC EMBODIMENTS

Figure 1:
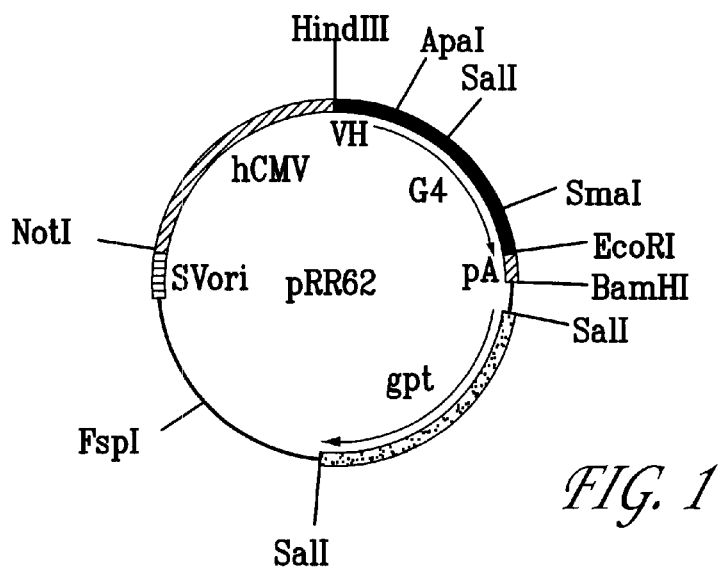
FIG. 1 is a schematic diagram of plasmid pRR62.

The following description of certain embodiments of the invention is provided by way of example only and is not to be regarded as placing any limitation on the scope of the protection claimed.

Molecular Cloning and Construction of the CTMO1 Chimeric Heavy Chain

The heavy chain variable domain of CTMO1 was cloned using the polymerase chain reaction. This enabled the construction of the chimeric version in a single step as described below.

Polyadenylated RNA was isolated from the CTMO1 hybridoma cell line using the guanidinium isothiocyanate/lithium chloride method [17]. Double stranded cDNA was synthesised and used as a template for PCR amplification of the VH gene. A set of twenty four 5' forward primers were synthesised to complement a sequence within the murine leader sequence of VH domains [16] and to introduce a BstEII restriction site. A set of twelve 3' reverse primers was synthesised to complement the framework 4 region of VH [20] and included an ApaI restriction site.

The sequence of the basic 5' primer is given in the Sequence Listing as ID No. 3. The set of twenty four primers was based on this primer as follows. In one group of twelve primers, residue 27 remained as C. In three subgroups of four primers, residue 25 either remained as G or is altered to C or T. In each subgroup, the four primers differed at residue 28, which was A, C, G or T. In the subgroups where residue 25 is C or T, the sixth amino acid is His.

In the second group of twelve primers, residue 27 is changed to G. In three subgroups of four primers, residue 25 either remains as G or is altered to C or T. In each subgroup, the four primers differed at residue 28, which was A, C, G or T. Where residue 25 is C or G, amino acid 6 is Gln and where residue 25 is T, amino acid residue 6 is His. Where residue 28 is T or C, amino acid residue 7 is Cys. Where residue 28 is G, amino acid residue 7 is Trp.

The sequence of the basic 3' PCR primer is given in the Sequence Listing as ID No. 4. The set of twelve primers was based on this primer as follows. Residue 5 could remain as G or could be altered to A or T. Residue 11 either remains as A or is altered to G. Residue 12 either remains as A or is altered to C.

PCR amplification of CTMO1 VH was carried out using the following conditions:

10 pmoles each primer; 20 ng cDNA; 0.5 U Taq polymerase; 94° C. 1 min; 50° C. 2 min; 72° C. 3 min; for 40 cycles.

The PCR amplified VH fragment was restricted with BstEII and ApaI and ligated to an adaptor to reconstruct the leader sequence and add a 5' HindIII restriction enzyme site. The sequence of the adaptor used is given in the Sequence Listing as Sequence ID No. 5 and codes in part for the leader amino acid sequence of the VH domain of the murine anti TAG-72 monoclonal antibody B72.3 (WO-A-89/01783).

The adapted fragment was then cloned into the HindIII/ApaI sites of the vector pE1004 to give plasmid pRR62 shown in FIG. 1. Plasmid pRR62 consists of an SV40 origin of replication followed by the hCMV-MIE promoter/enhancer region. The promoter/enhancer controls a nucleotide sequence encoding a chimeric heavy chain comprising the CTMO1 heavy chain variable domain fused to human g4 constant domains. Downstream of the coding sequence is a poly A site and gpt gene.

The heavy chain variable region of several independent clones of pRR62 were sequenced. The DNA sequence and deduced amino sequence for CTMO1 VH are given in Sequence ID No. 1.

Molecular Cloning and Construction of the CTMO1 Chimeric Light Chain

Polyadenylated RNA was isolated from the CTMO1 hybridoma cell line using the guanidinium isothiocyanate/lithium chloride method [17]. Double stranded cDNA was synthesised [21] and a cDNA library was constructed in plasmid pSP64 [22] using EcoRI linkers. A screening probe was synthesised, complementary to mouse immunoglobulin light chain constant region by PCR amplification. The light chain probe was a 318 bp PCR fragment encoding the mouse kappa light chain constant region [23].

The probe was radio-labelled ($g^{32}P$) ATP by random hexanucleotide priming and was used to screen the cDNA library.

The clone which encoded the complete leader, variable and constant domains of light chain was isolated and designated as pRB63.

A fragment of pRB63, which encodes the variable domain of the light chain was recovered by PCR amplification. The PCR primers introduced a BstbI and SplI restriction sites at the 5' and 3' ends of the VL region respectively to enable subsequent cloning of the fragment.

Figure 2:
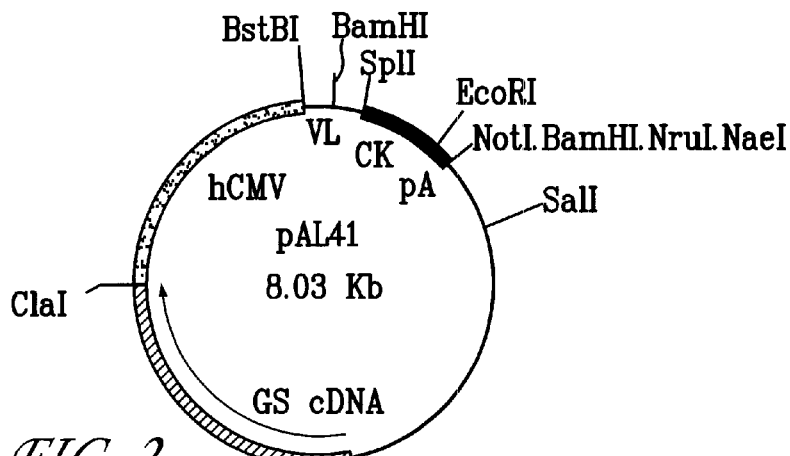
FIG. 2 is a schematic diagram of plasmid pAL41.

The PCR amplified fragment of plasmid pRB63 was restricted with BstbI/SplI and ligated between the BstbI/SplI sites of plasmid pMRR010 to produce plasmid pAL41, which is shown in FIG. 2. Plasmid pAL41 consists of a glutamine synthetase cDNA having downstream of it the hCMV-MIE promoter/enhancer region. The promoter/enhancer region controls a nucleotide sequence encoding a chimeric light chain comprising the CTMO1 light chain variable domain fused to a human CK constant domain. Downstream of the coding sequence is a poly A site.

Nucleotide sequence analysis was carried out according to the chain termination procedure [24]. The VH coding sequence insert in pRR62 and the VL coding sequence insert in pAL41 were fully sequenced. The DNA and predicted amino acid sequences for the unprocessed variable domains of the CTM01 heavy and light chains are shown in the Sequence Listing appended to the end of the description as Sequence ID No. 1 and No. 2 respectively.

Sequence No. 1 shows the sequence coding for the VH domain and the predicted amino acid sequence. The leader sequence for the heavy chain runs from residue 1 to residue 19 as shown in Sequence No. 1. Sequence No. 2 shows the sequence coding for the VL domain together with the predicted amino acid sequence. The leader sequence for the light chain runs from residue 1 to residue 20 as shown in Sequence No. 2. Examination of the derived amino acid sequences revealed considerable homology with other characterised immunoglobulin genes. The CTM01 MAb was confirmed to be an IgG1-kappa antibody.

Preparation of Chimeric Antibody Products
Chimeric Light Chain Vector

Figure 3:
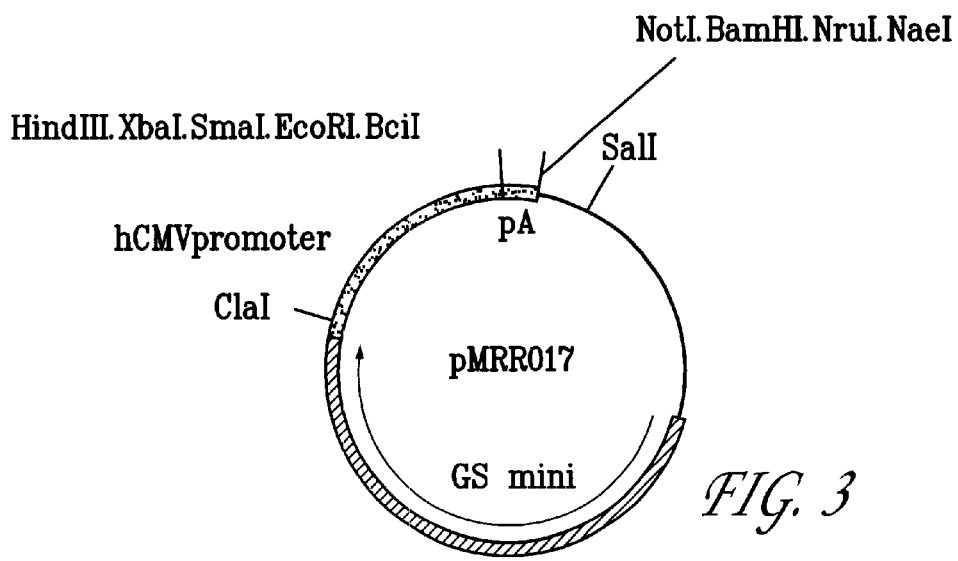
FIG. 3 is a schematic diagram of plasmid pMRR017.
Figure 4:
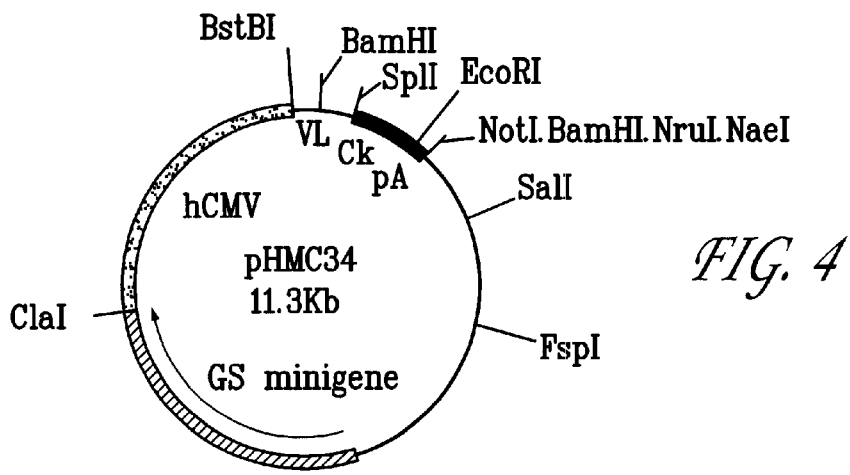
FIG. 4 is a schematic diagram of plasmid pHMC34.

A ClaI-EcoRI fragment of pAL41 carrying the hCMV promoter and chimeric light chain was cloned into plasmid pMRR017 which is shown in FIG. 3. Plasmid pMRR017 has a GS mini gene (WO-A-87/04462), hCMV-MIE promoter/enhancer region, a polylinker sequence and a poly A site. This produced plasmid pHMC34, which is shown in FIG. 4.

In plasmid pHMC34, the chimeric light chain gene is under the control of the hCMV-MIE promoter/enhancer sequence.

Chimeric Heavy Chain Vectors

IgG1 Construct

Figure 5:
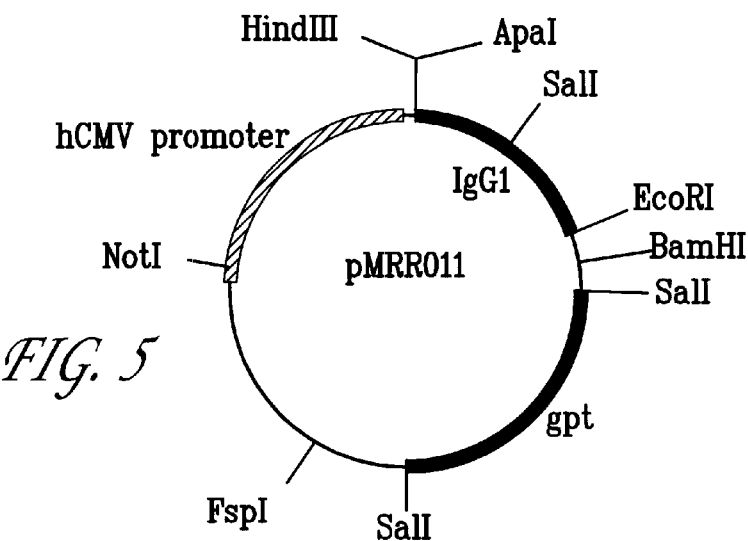
FIG. 5 is a schematic diagram of plasmid pMRR011.
Figure 6:
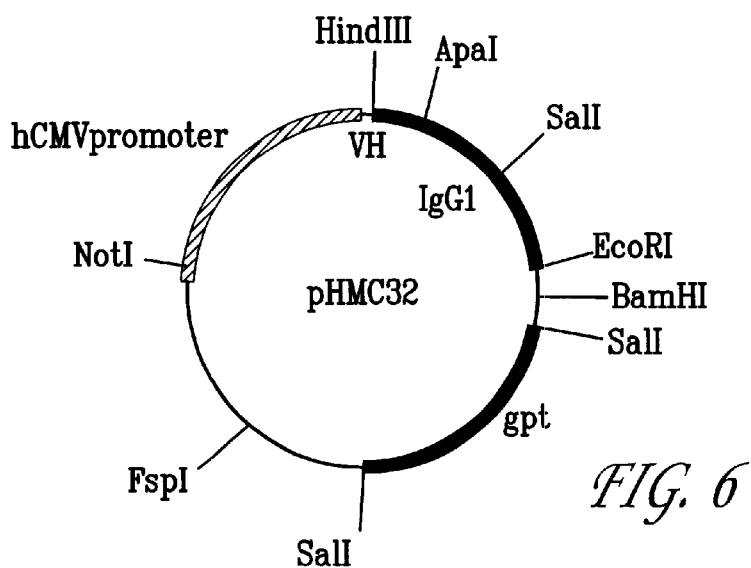
FIG. 6 is a schematic diagram of plasmid pHMC32.
Figure 7:
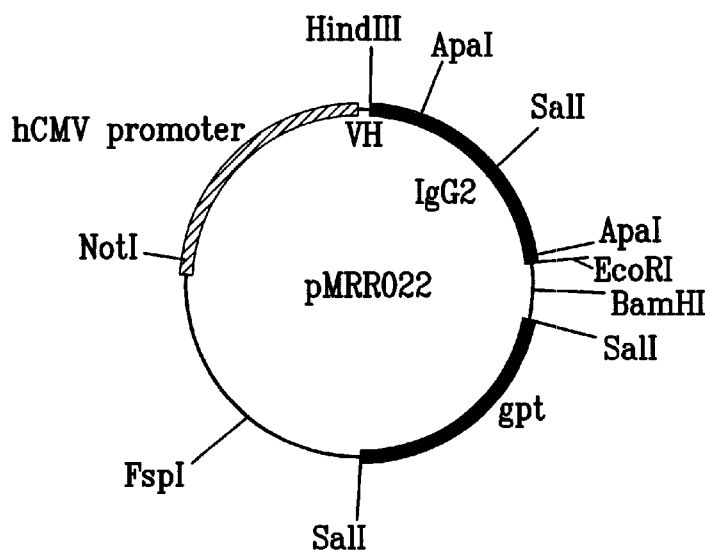
FIG. 7 is a schematic diagram of plasmid pMRR022.

A HindIII-ApaI fragment containing the sequence encoding the VH domain was excised from plasmid pRR62 (FIG. 1). This fragment was inserted between the HindIII and ApaI sites of plasmid pMRR011. Plasmid pMRR011 is shown in FIG. 5 and comprises an hCMV-MIE promoter/enhancer region, an SV40 polyadenylation sequence, a gpt gene and a sequence encoding a human IgG1 heavy chain lacking a variable domain. The plasmid thus produced, pHMC32, is shown in FIG. 6 and has a chimeric heavy chain coding sequence under the control of the hCMV-MIE promoter/enhancer. The chimeric heavy chain has the VH domain from the CTMO1 MAb fused to human IgG1 constant domains.

IgG2 Construct

The HindIII-ApaI fragment of pRR62 (FIG. 1) was inserted between the HindIII and ApaI sites of a plasmid containing an hCMV-MIE promoter, a polylinker site and a nucleotide coding sequence which encodes the three constant domains of a human IgG2 antibody. This yielded plasmid pMRR022 which encodes a chimeric heavy chain having the CTM01 variable domain linked to the human IgG2 constant domains.

IgG4 Construct

Figure 8:
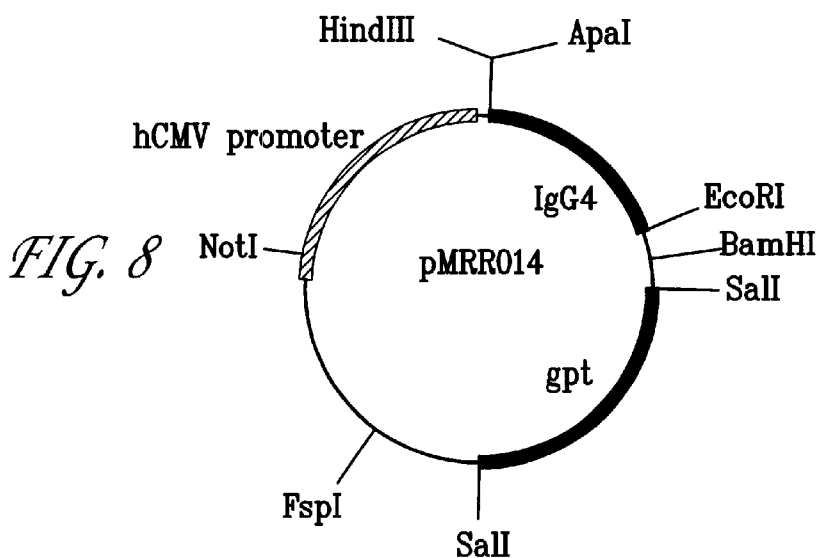
FIG. 8 is a schematic diagram of plasmid pMRR014.
Figure 9:
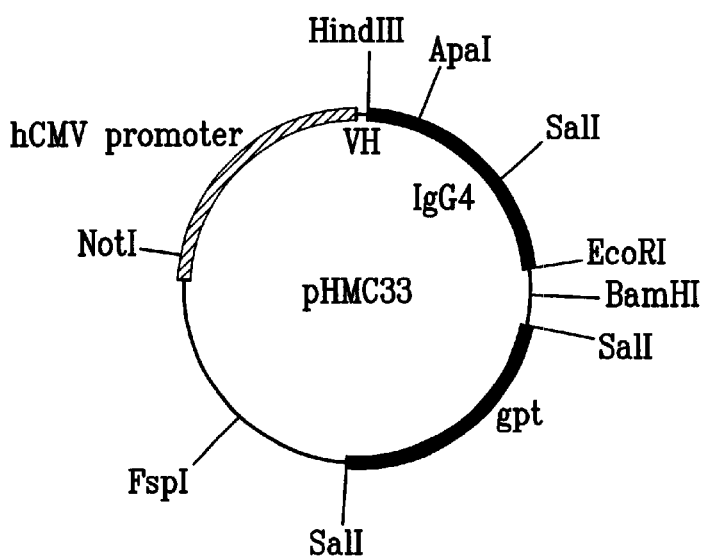
FIG. 9 is a schematic diagram of plasmid pHMC33.

The HindIII-ApaI fragment of pRR62 (FIG. 1) was inserted between the HindIII and ApaI sites of plasmid pMRR014 to produce plasmid pHMC33. Plasmids pMRR014 and pHMC33 are shown in FIGS. 8 and 9 respectively. Plasmid pMRR014 has an hCMV-MIE promoter, a polylinker site and a nucleotide coding sequence which encodes the three constant domains of a human IgG4 antibody. Plasmid pHMC33 is identical to plasmid pHMC32 except that the coding sequence encodes a chimeric heavy chain having the CTM01 variable domain and human IgG4 constant domains in place of the human IgG1 constant domains.

Altered IgG4 Construct

Figure 10:
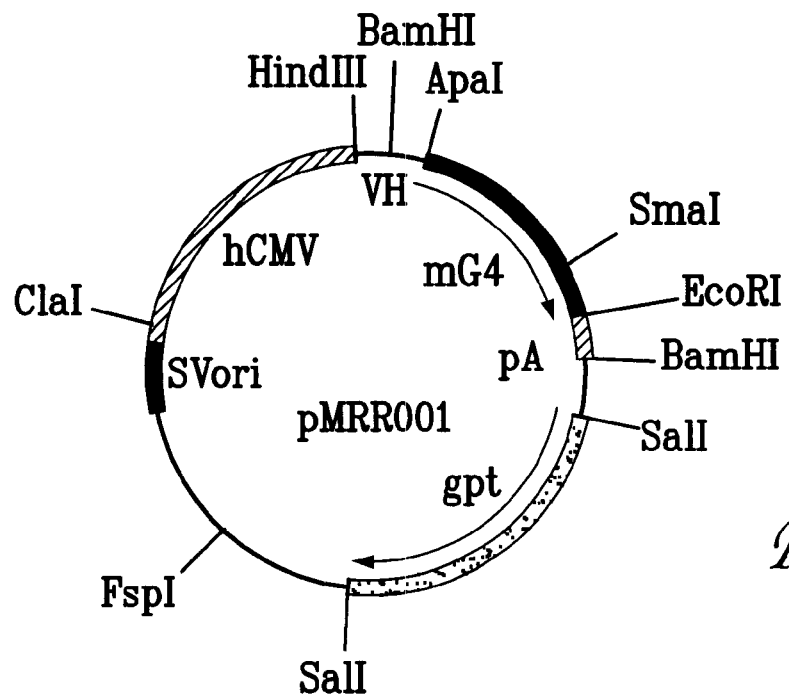
FIG. 10 is a schematic diagram of plasmid pMRR001.

The HindIII-ApaI fragment was reisolated from plasmid pHMC33. Plasmid pMRR001 shown in FIG. 10 was digested with HindIII and ApaI. The large fragment was isolated and ligated to the HindIII-ApaI fragment of pHMC33 to produce plasmid pHMC35, shown in FIG. 11. Plasmid pHMC35 is almost identical to plasmid pHMC32 except that the coding sequence encodes a chimeric heavy chain having the CTM01 variable domain and altered human IgG4 (hereinafter referred to as IgG4P) constant domains in place of the human IgG1 constant domains.

The alteration in the constant domains comprises a change of a serine residue in the hinge region at position 241 to a proline residue. This change advantageously abolished the formation of an 80 KD half antibody which otherwise occasionally is formed with IgG4 constant domains.

Chimeric Heavy and Light Chain Vectors

Vectors were constructed having operons coding for both heavy and light chains within the same vector.

Figure 11:
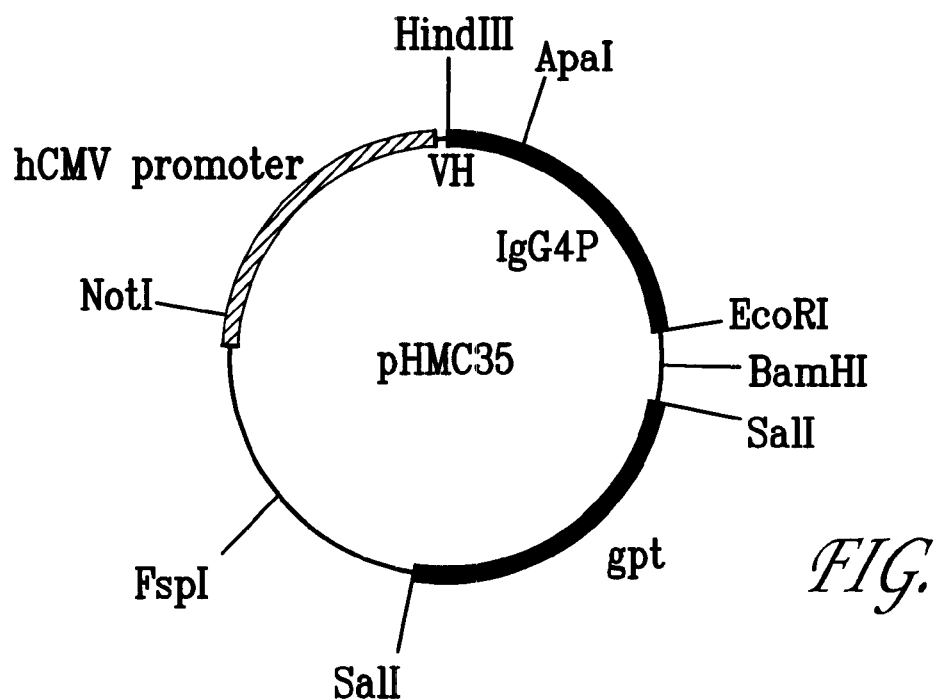
FIG. 11 is a schematic diagram of plasmid pHMC35.

A NotI-SalI fragment carrying the hCMV-MIE promoter/enhancer, the chimeric light chain encoding sequence and the SV40 poly A site together with the GS mini gene was excised from plasmid pHMC34 (FIG. 4). A NotI-HindIII fragment carrying the hCMV-MIE promoter/enhancer was excised from plasmid pHMC35 (FIG. 11). A HindIII-SalI fragment carrying the altered IgG4 heavy chain coding sequence and SV40 poly A site was excised from plasmid pHMC35 (FIG. 11). These three fragments were ligated together to produce plasmid pHMC38, which is shown in FIG. 12, and codes for expression of chimeric light chain together with the altered IgG4 chimeric heavy chain.

Plasmids pHMC32, pMRR022 and pHMC33 were digested with HindIII and EcoRI and the fragments containing the chimeric heavy chain encoding sequences were isolated. The isolated fragments were each ligated with the large HindIII-SalI fragment of pHMC38 (FIG. 12) and an EcoRI-SalI fragment comprising the SV40 poly A region. The ligations produced plasmids pHMC40, pHMC41 and pHMC42 (shown in FIGS. 13 to 15 respectively). pHMC40 encodes a heavy chain having IgG1 constant domains. pHMC41 encodes IgG2 constant domains and pHMC42 encodes IgG4 constant domains.

Preparation of CDR-Grafted Antibody Products

It was decided to use the EU human antibody framework [16] for carrying out the CDR-grafting. The strategy followed for CDR-grafting was as set out in our International Patent Specification No. WO-A-91/09967.

Two CDR-grafted heavy chains were designed. In the first, gH1, all three CDRs [as defined by Kabat, ref. 16] were changed to murine residues. In addition, residues 2, 37, 71, 73, 94, 103, 104, 105 and 107, which are outside the Kabat CDRs, were also changed to murine residues. In the second, gH2, in addition to those murine residues in gH1, residues 48, 67 and 69 were changed to murine residues with a view to improving packing of the VH domain.

Two CDR-grafted light chains were also designed. In the first, gL1, all three CDRs [as defined by Kabat, ref. 16] were changed to murine residues. In addition residues 3, 36, 63 and 108, which are outside the Kabat CDRs, were changed to murine resides. In the second, gL2, in addition to those murine residues in gL1, residues 37, 45 and 48 were changed to murine residues with a view to improving packing.

Figure 16:
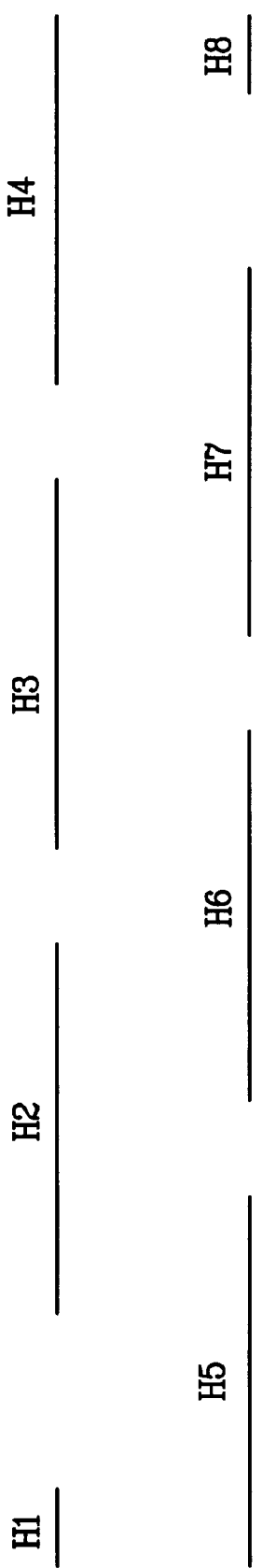
FIG. 16 shows the alignment of oligonucleotides H1 to H8 in the formation of the gH1 coding sequence.

A nucleotide sequence coding for the gH1 variable domain was produced by oligonucleotide assembly using oligonucleotides H1 to H8. The sequences for these oligonucleotides are given in the Sequence Listing at the end of the description under Sequence ID Nos. 6 to 13. The way in which these oligonucleotides are assembled to produce the gH1 coding sequence is shown in FIG. 16. The amino acid sequence coded for by this gH1 sequence is shown in the sequence listing under Sequence ID No. 14.

A nucleotide sequence coding for the gH2 variable domain was also produced by oligonucleotide assembly using oligonucleotides H1, H2, H3A, H4, H5, H6A, H7 and H8. Oligonucleotide H3A differs from oligonucleotide H3 (Sequence ID No. 8) in that residues 55 to 57 have been changed from GTG to GCA and residues 61 to 63 have been changed from ATT to CTG. Oligonucleotide H6A differs from oligonucleotide H6 (Sequence ID No. 11 ) in that residues 70 to 72 have been changed from TAC to TAA. Thus, the gH2 variable domain encodes the same sequence as is shown under Sequence ID No. 14, except that at residue 67, MET has been changed to ILE; at residue 87, VAL has been changed to ALA; and at residue 89, ILE has been changed to LEU.

A nucleotide sequence coding for the gL1 variable domain was produced by oligonucleotide assembly using oligonucleotides L1 to L8. The sequences for these oligonucleotides are given in the Sequence Listing at the end of the description under Sequence ID Nos. 15 to 22. The way in which these nucleotides are assembled is similar to that shown in FIG. 16 for the gH1 coding sequence (except that L is substituted for H). The amino acid sequence coded for by the assembled gL1 variable domain coding sequence is shown in the Sequence Listing under Sequence ID No. 23.

A nucleotide sequence coding for the gL2 variable domain was produced by oligonucleotide assembly using oligonucleotides L1, L2A, L3A and L4 to L8. Oligonucleotide L2A differs from oligonucleotide L2 (Sequence ID No. 16) in that residues 28 to 30 have been changed from CAG to GTA. Oligonucleotide L3A differs from oligonucleotide L3 (Sequence ID No. 17) in that residues 25–27 have been changed from CAG to CTC, residues 49–52 have been changed from AAG to CAG and residues 59–61 have been changed from CAT to ATC. Thus, the gL2 variable domain encodes the same sequence as is shown under Sequence ID NO. 23, except that: at residue 23, Gln has been changed to Val; at residue 62, Gln has been changed to Leu; at residue 60, Lys has been changed to Gln; and at residue 73, Met has been changed to Ile.

For gene assembly 1 pmol of H2–H7 or L2–L7 was mixed with 10 pmol or H1 and H8 or L1 and L8 in a 100 ml reaction with 5U Taq polymerase. A PCR reaction was done using 30 cycles (95° C., 1 min. 50° C. 1 min; 72° C. 1 min). The resulting fragments were cut with HindIII and Apal for VL with Bstb1 and SPII for VH.

Figure 17:
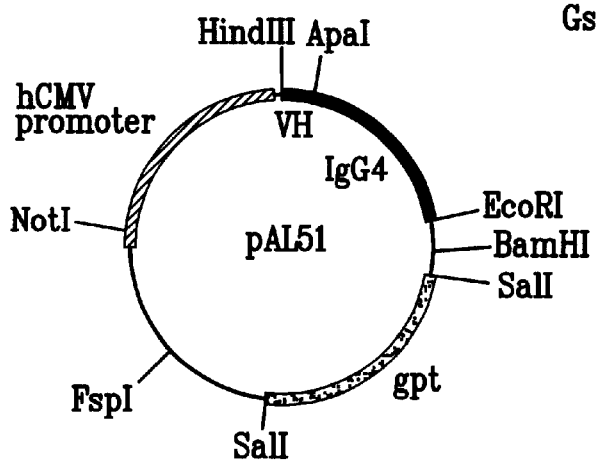
FIG. 17 is a schematic diagram of plasmid pAL51.
Figure 18:
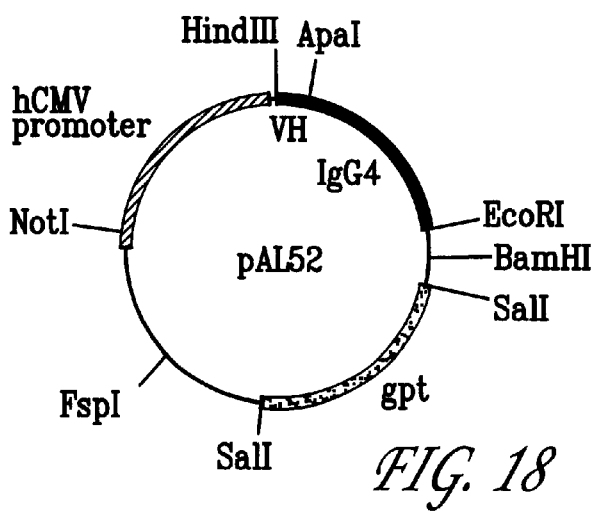
FIG. 18 is a schematic diagram of plasmid pAL52.

The nucleotide sequences coding for gH1 and gH2 were cloned as HindIII-Apal fragments into plasmid pMRR014 (FIG. 8) to produce plasmids pAL51 and pAL52 (FIG. 17 and 18 respectively).

Figure 20:
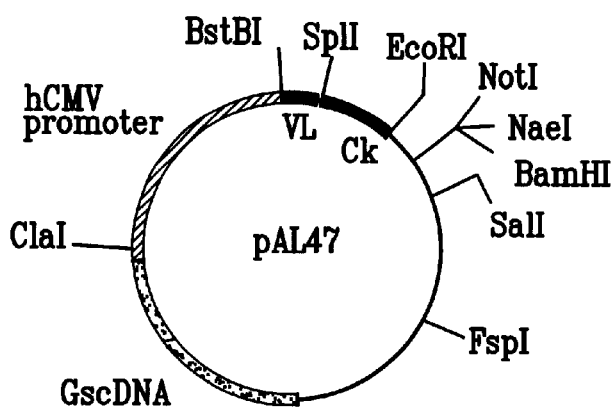
FIG. 20 is a schematic diagram of plasmid pAL47.
Figure 21:
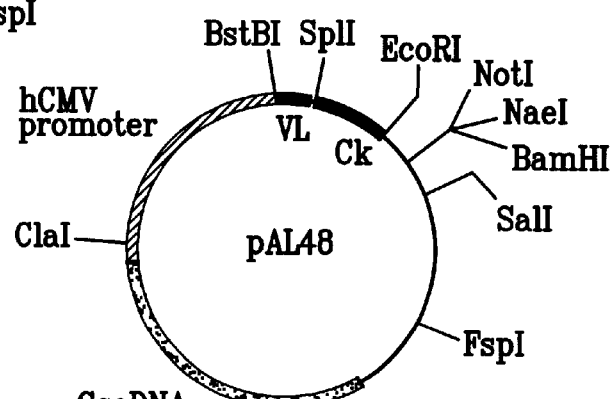
FIG. 21 is a schematic diagram of plasmid pAL48.
Figure 19:
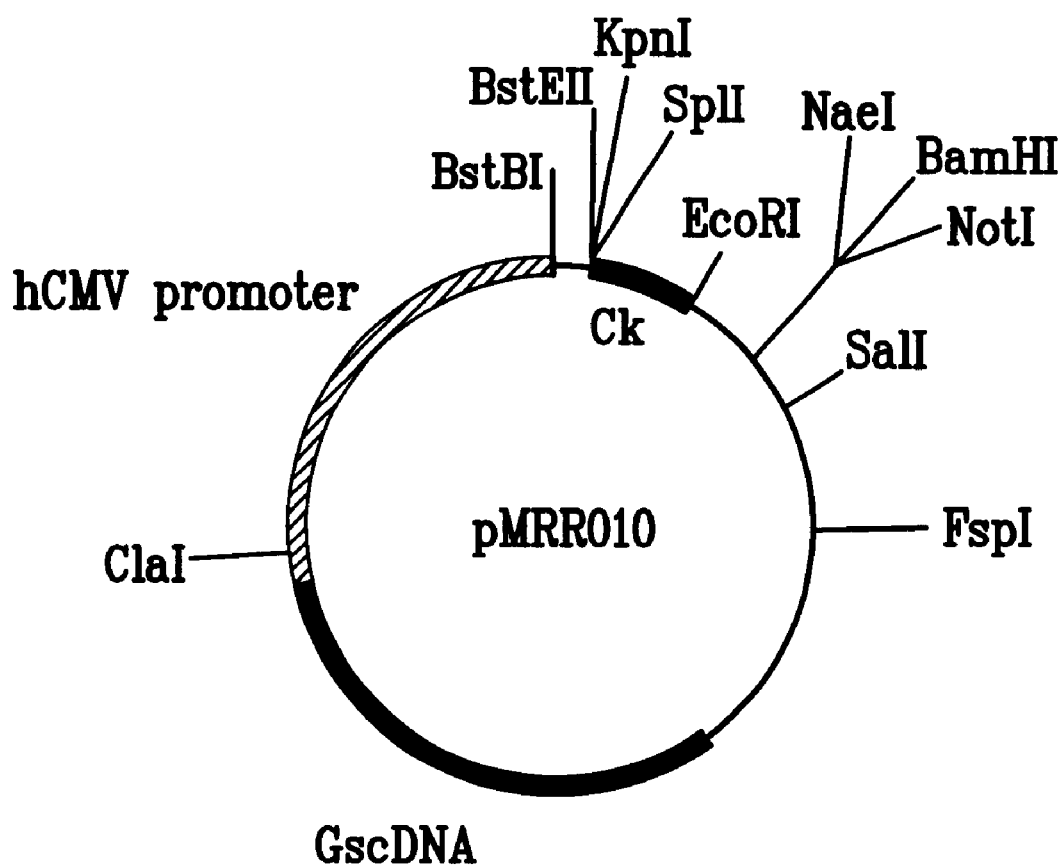
FIG. 19 is a schematic diagram of plasmid pMRR010.

The nucleotide sequences coding for gL1 and gL2 were cloned as HindIII-Apal fragments into plasmid pMRR010 (FIG. 19) to produce plasmids pAL47 and pAL48 (FIGS. 20 and 21 respectively).

Transient Expression of Chimeric/Chimeric or CDR-Grafted/Chimeric Antibodies

The following plasmids:
pHMC38, pHMC40, pHMC41 and pHMC42
and the following pairs of plasmids:
pAL47, pHMC33; pAL48, pHMC33; pAL51, pAL41; pALS52,
pAL41; and pAL48, pAL41:
were each transfected or cotransfected into CHO-L761h cells for transient expression.

Assembly ELISA assays on culture supernatants resulting from the single transfected cells showed that they contained assembled antibody.

The assembly ELISA assay for quantifying antibody yields used microwell plates coated with a goat F(ab')$_2$ anti-human IgGFc. Following incubation with transfected culture supernatants, bound chimeric or CDR-grafted antibody was revealed with a horseradish peroxidase (HRP)-conjugated murine anti-human IgK antibody using tetramethyl benzidine (TMB) as the substrate. Concentrations of chimeric or CDR-grafted whole antibody in the samples were interpolated from a calibration curve generated from serial dilutions of purified chimeric B72.3 γ4 antibody [25].

Binding Activity of Transiently Expressed Chimeric or CDR-Grafted Antibodies

Direct binding ELISA assays for determining the binding activity of the transiently expressed antibodies were carried out as follows.

An affinity column was prepared by attaching the CTM01 MAb to a suitable chromatographic medium in conventional manner. In a first method, pooled human urine samples were applied directly to the affinity column. In a second method, human milk was subjected to low speed centrifugation to separate the cream from skimmed milk. The skimmed milk was then subjected to high speed centrifugation to produce an aqueous and a lipid component. The aqueous component was applied to the affinity column.

Once the affinity column was loaded, by either of the two methods, column fractions were eluted at high and low pHs, neutralised and assayed for reactivity with the CTM01 MAb. Fractions showing reactivity were pooled and dialysed. The pooled fractions contained the polymorphic epithelial mucin (PEM) recognised by the CTM01 MAb.

Microwell plates were coated with PEM obtained as described above. The microwells were then incubated with serial dilutions of culture supernatants. Binding of chimeric or CDR-grafted antibody was revealed and quantified by use of an HRP-conjugated murine anti-human IgK antibody.

The results of direct binding ELISA assays on the supernatants from singly transfected cells are shown in FIG. 22. These assays confirm that all the supernatants contained antibodies capable of binding to PEM. No significant differences in binding activity were observed.

The direct binding ELISA assays on the supernatants from doubly transfected cells confirmed that the supernatants contained antibodies capable of binding to PEM and that the chimeric/chimeric antibody bound better than any of the CDR-grafted/chimeric antibodies.

A competition binding assay was carried out using polystyrene beads coated with PEM obtained as described above. CTM01 MAb was radiolabelled with 125I and was used to compete with the antibody produced by the pHMC40 (IgG1) transfected cells. The potency of the chimeric antibody was 84–102% that of the CTM01 MAb.

Transient Expression of CDR-Grafted Antibodies

The following pairs of plasmids:

pAL47, pAL51; pAL47, pAL52; pAL48, pAL51; and pAL48, pAL52;

were cotransfected into CHO-L761 cells.

Direct binding assays were carried out on the culture supernatants produced by the doubly transfected cell lines.

The results of these assays are shown in FIG. 23, together with some results for chimeric/CDR-grafted antibodies.

From all the direct binding assays referred to above, it can be determined that the order of binding activity of the various antibodies produced by transient expression is as follows:

cLcH3>gL1cH=gL1gH2>cLgH2=gL2H2=gL1gH1=gL2cH>gL2gH1.

(wherein:

cL=chimeric light chain;

cH=chimeric heavy chain gL1=CDR-grafted light chain with lowest number of amino acid changes;

gL2=CDR-grafted light chain with highest number of amino acid changes;

gH1=CDR-grafted heavy chain with lowest number of amino acid changes;

gH2=CDR-grafted heavy chain with highest number of amino acid changes).

The more active variants (cLcH, gL1cH, gL1gH2 and gL2gH2) together with the CTM01 MAb were tested in a competition enzyme immunoassay (EIA). Microwell plates were coated with PEM obtained as described above. The CTM01 MAb was biotinylated and was used to compete with the four variants referred to above. Bound biotinylated CTM01 MAb was revealed and quantified using a streptavidin-HRP conjugate and TMB.

Figure 24:
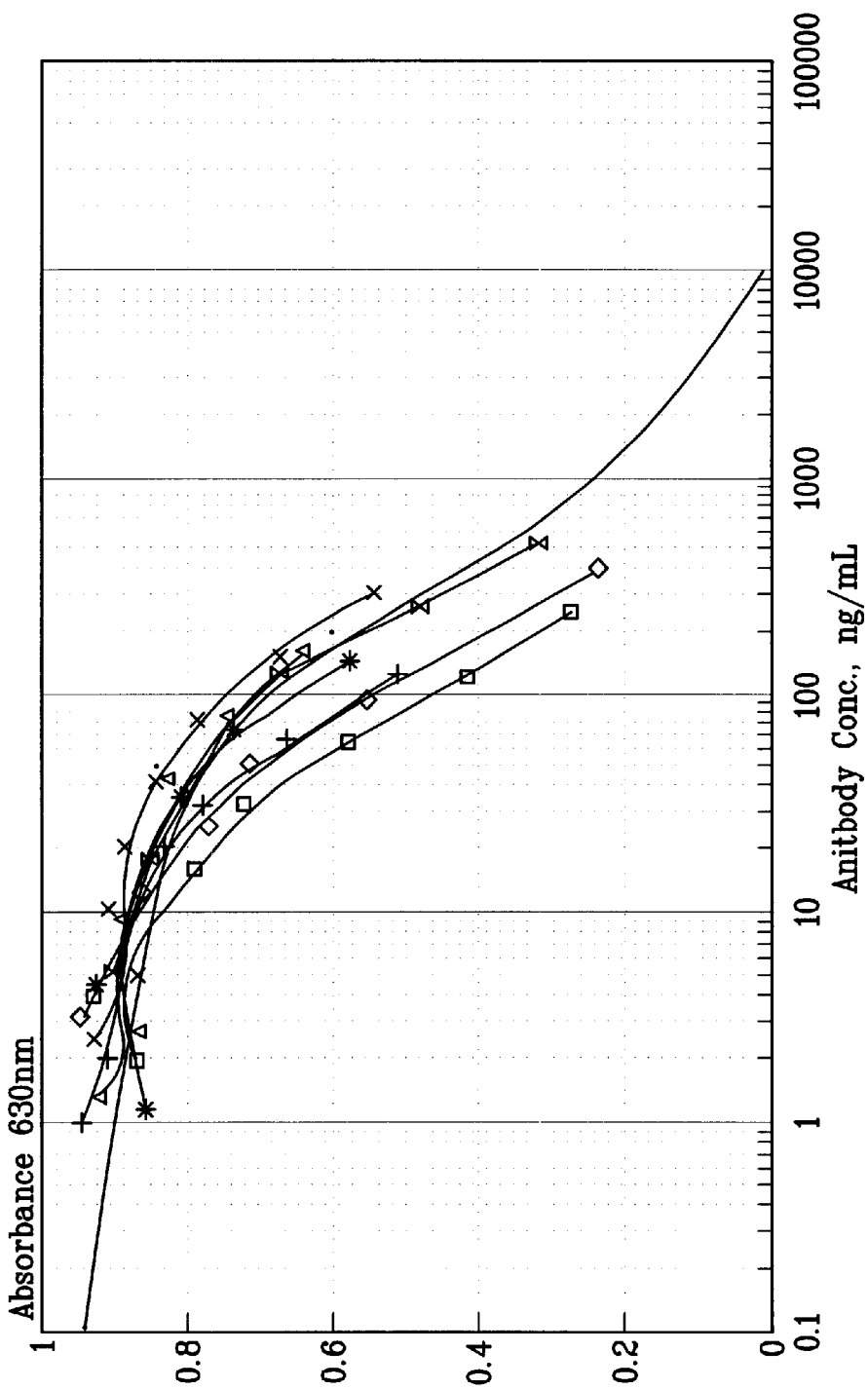
FIG. 24 is a graph of a competition EIA on transiently expressed chimeric and CDR-grafted antibodies.

The results of the competition EIA are shown in FIG. 24, which shows the same ranking of binding activity as set out above, except that the gL1cH combination shows greater activity than the cLcH combination.

It can thus be seen that chimeric, chimeric/CDR-grafted and CDR-grafted antibodies which recognise the same antigen as the CTM01 MAb have successfully been produced.

In Vitro Cell Binding and Internalisation of CDR-Grafted CTM01 Antibodies

Stable NSO cell lines expressing gL1gH2IgG2 CTMO1 (hereinafter hu1:CTMO1) and gL1gH2IgG4P CTMO1 (hereinafter hu:CTMO1) antibody variants were made by transfecting into NSO cells by electroporation double gene expression plasmids assembled by ligating the large (7.8 kbp) Not1/BamH1 fragment of pAL47 to the 2.4 kbp Not1/Apa1 fragment from pAL52 and either a 1.9 Kbp BamH1/Apa1 (partial) fragment carrying the IgG2 constant domains or a 2 kbp Apa1/BamH1 fragment carrying the IgG4P constant domains as appropriate.

Antibody, purified from the supernatant of each cultured cell line by protein-A sepharose chromatography was radio-labelled ($^{125}$I) and incubated using a conventional continuous exposure method with either MX-1 or MCF-7 breast carcinoma cells. Radiolabelled murine CTMO1 was used in all tests as a comparison. All antibodies were incubated at 2 μg/million cells. The total binding of antibodies to the cells and the peak net uptake of the antibodies by the cells was determined. The results are shown in Table 1 below. With both cell lines each CDR grafted antibody exhibited better binding and internalisation than the murine form.

TABLE 1

| Antibody | Cell Line | Total Binding, 0° (molecules/cell) | Peak Net Uptake (molecules/cell) |
| --- | --- | --- | --- |
| hu1:CTMO1 | MCF-7 | 650,000 | 150,000 |
| hu:CTMO1 | MCF-7 | 450,000 | 90,000 |
| Murine CTMO1 | MCF7 | 300,000 | 70,000 |
| hu1:CTMO1 | MX-1 | 1,200,000 | 150,000 |
| hu:CTMO1 | MX-1 | 1,100,000 | 150,000 |
| Murine CTMO1 | MX-1 | 800,000 | 80,000 |

In Vivo Anti-Tumour Activity of A Conjugate of hu:CTMO1 and an Anti-Tumour Antibiotic hu:CTMO1 was conjugated to the hydroxysuccinimide derivative of 4-mercapto-4-methyl-pentanoic acid disulphide of N-acetyl calicheamicin $_{\gamma 1}{}^I$ as follows:

Synthesis of the 4-Mercapto-4-Methyl-Pentanoic Acid Disulphide Derivative of N-acetyl Calicheamicin $_{\gamma 1}{}^I$

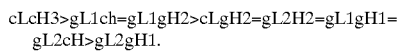

To N-acetyl calicheamicin $_{\gamma 1}{}^I$ [U.S. Pat. No. 5,079,233] at a concentration of 2 mg/mL in acetonitrile at −15° C. was added 5 molar equivalents of 4-mercapto-4-methyl-pentanoic acid and 6 molar equivalents of triethylamine. After 24 hours at −15° C. the reaction was checked by $C_{18}$-HPLC. [If the reaction is incomplete, additional amounts of 4-mercapto-4-methyl-pentanoic acid and triethylamine are added]. Upon completion of the reaction the volatile organics were evaporated under reduced pressure and the crude product was chromatographed on Bio-Sil A using a gradient of 1 to 5% methanol in chloroform. Pure fractions as assessed by tlc were pooled and evaporated to a glass. The $^1$H-NMR of the product was similar to N-acetyl calicheamicin $_{\gamma 1}{}^I$, but was missing the absorbance for -SSSMe and exhibits absorbances for the methylpentanoic acid moiety as expected. FAB-MS gave m/z=1478 (M+H) and 1500 (M+Na).

Synthesis of the Hydroxysuccinimide Derivative of 4-Mercapto-4-Methyl-Pentanoic Acid Disulphide of N-Acetyl Calicheamicin $_{\gamma 1}{}^I$ To the 4-mercapto-4-methyl-pentanoic acid disulphide derivative of N-acetyl calicheamicin $_{\gamma 1}{}^I$ described above at a concentration of 5 mg/mL in acetonitrile at ambient temperature was added 3 molar equivalents of N-hydroxysuccinimide and 5 molar equivalents of 1-(3-dimethylamino-propyl)-3-ethylcarbodiimide hydrochloride. After 1 hour the reaction was checked by $C_{18}$-HPLC. {If the reaction is incomplete, then additional 1-(3-dimethylaminopropyl)-3-ethylcarbodiimide hydrochloride is added]. Upon completion of the reaction the volatile organics were evaporated under reduced pressure and the crude product was chromatographed on Bio-Sil A using a gradient of 0 to 5% methanol in chloroform. Pure fractions as assessed by tlc were pooled and stripped to a glass. The $^1$H-NMR was similar to that of the product described above, but with absorbances present for succinimide, as expected. FAB-MS gave m/z=1575 (M+H) and 1597 (M+Na).

Synthesis of hu:CTMO1 Conjugate Using the Hydroxysuccinimide Derivative of 4-Mercapto-4-Methyl-Pentanoic Acid Disulphide of N-Acetyl Calicheamicin $_{\gamma 1}{}^I$ To hu:CTMO1 in phosphate buffer at a pH of about 7.4 was added 2–6 molar equivalents of the hydroxysuccinimide derivative of 4-mercapto-4-methyl-pentanoic acid disulphide of n-acetyl calicheamicin $_{\gamma 1}{}^I$, described above, in dimethylformamide (DMF) such that the final concentration of DMF was 10–15%. After completion of the reaction (2–24 hours) the low-molecular-weight organic material was removed by passing through a desalting column using pH 7.4 phosphate buffer. The product was further purified by chromatography on a gel exclusion column and concentrated to give a monomeric product with an average loading of 1–3 molecules of calicheamicin derivative per molecule of antibody.

In Vivo Test for Antitumour Activity

Figure 25:
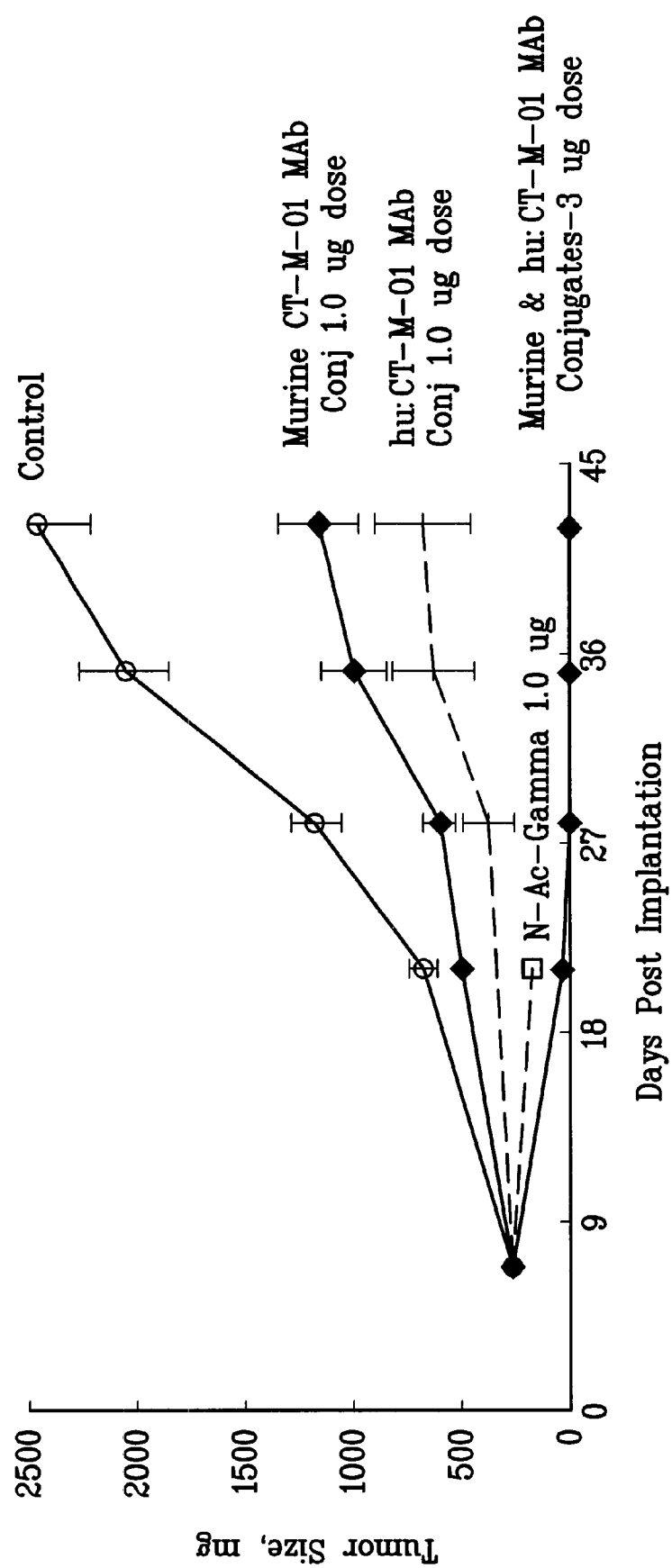
FIG. 25 is a graph comparing the effects on tumour size obtained by treating nude mice implanted with a human ovarian xenograft tumour with a humanised CDR grafted CTMO1 and a murine CTMO1 antibody each conjugated to the hydroxysuccinimide derivative of 4-mercapto-4-methylpentanoic acid disulphide of N-acetyl calicheamicin $\gamma 1^I$.

The human ovarian xenograft tumour, OvCar3, implanted subcutaneously in nude mice was used as a test system to study the efficacy of the hu:CTM01 conjugate in vivo. A murine CTMO1 conjugate containing the same calicheamicin was also tested for comparison. Tumours were implanted subcutaneously into athymic mice and test samples were inoculated intraperitoneally (IP) at several dose levels on a q4 day×3 schedule, starting 2–3 days after tumour implantation with 6 mice per group and 10 in each control group. Tumour mass was determined by measuring the tumour diameter once weekly during 42 days post tumour implantation. Significant antitumour activity was defined as a sustained 58% inhibition of mean tumour mass compared with untreated controls in groups with grater than 65% survivors. At both the 1 and 3 µg doses of drug equivalents the hu:CTMO1 conjugate showed significant inhibition of tumour growth (FIG. 25). No deaths were noted in the 42 days observation period in any test group. In all test groups, n=6, in the control group n=10, error bars=± Standard Error Mean for each data point.

REFERENCES

1. Kohler & Milstein, Nature 265, 495–497, 1975
2. Begent et al, Br. J. Cancer, 62, 487, 1990
3. Verhoeyen et al, Science, 293, 1534–1536, 1988
4. Riechmann et al, Nature 332, 323–327, 1988
5. Queen et al, Proc. Natl. Acad. Sci., USA, 86, 10029–10033, 1989 and WO-A-90/078861
6. Tempest et al, Biotechnology, 9, 266–271, 1991
7. Co et al, Proc. Natl. Acad. Sci., USA, 88, 2869–2873, 1991
8. Verhoeyen et al, 1991 in Epenetos, A.A., (ed.),—"Monoclonal Antibodies: Applications in Clinical Oncology"
9. Gorman et al, Proc. Natl,. Acad. Sci., USA, 88, 4181–4885, 1991
10. Ehrlich, P., Collected Studies on Immunity, 2, John Wiley & Sons, New York, 1986
11. Levy & Miller, Ann. Rev. Med., 34, 107–116, 1983
12. Schlom & Weeks, Important Advances in Oncology, 170–192, Wippincott, Philadelphia, 1985
13. Sahagan et al, J. Immunol., 137, 3, 1066–1074, 1986
14. Nishimura et al, Cancer Res., 47, 999–1005, 1987
15. Aboud-Pirak et al, Cancer Res., 48, 3188–3196, 1988
16. Kabat et al, Sequences of Proteins of Immunological Interest, US Department of Health and Human Services, NIH, USA, 1987 and Wu, T. T. and Kabat, E. A. J. Exp. Med., 132, 211–250, 1970
17. Maniatis et al, Molecular Cloning, Cold Spring Harbour, N.Y., 1982.
18. Primrose and Old, Principles of Gene Manipulation, Blackwell, Oxford, 1980
19. Jones et al, Nature, 54, 75–82, 1986
20. Orlandi et al, Proc. Natl. Acad. Sci., USA, 86, 3833–3837, 1989
21. Gubler and Hoffman, Gene, 25, 263–269, 1983
22. Melton et al, Nuc. Acids. Res., 12, 7035–7056, 1984
23. Max et al, J. Biol. Chem., 256, 5116–5120, 1981
24. Sanger et al, PNAS, 74, 5463–5467, 1977
25. Colcher et al, Proc. Natl. Acad. Sci., USA, 86, 3833–3837, 1989.

What is claimed is:

1. An antibody molecule having specificity for human milk fat globule (HMFG) comprising a humanized heavy chain having at least a variable region and a humanized complementary light chain having at least a variable region, wherein the heavy chain variable region comprises the amino acid sequence of SEQ ID NO:14.

2. An antibody molecule having specificity for human milk fat globule (HMFG) comprising a humanized light chain having at least a variable region and a humanized complementary heavy chain having at least a variable region, wherein the light chain variable region comprises the amino acid sequence of SEQ ID NO:23.

3. An antibody molecule having specificity for human milk fat globule (HMFG) comprising a humanized heavy chain having at least a variable region and a humanized complementary light chain having at least a variable region, wherein the heavy chain variable region comprises the amino acid sequence of SEQ ID No: 14 and the light chain variable region comprises the amino acid sequence of SEQ ID NO:23.

* * * * *